United States Patent
Yamamoto et al.

(10) Patent No.: US 8,546,586 B2
(45) Date of Patent: Oct. 1, 2013

(54) PYRAZOLE-BASED CYANINE DYE CONTAINING QUATERNARY AMMONIUM CATION

(75) Inventors: Naoyuki Yamamoto, Hyogo (JP); Tatsuo Kurosawa, Hyogo (JP); Satoshi Hasaba, Hyogo (JP); Matsuhiro Date, Hyogo (JP)

(73) Assignee: Wako Pure Chemical Industries, Ltd., Osaka-shi, Osaka (JP)

( * ) Notice: Subject to any disclaimer, the term of this patent is extended or adjusted under 35 U.S.C. 154(b) by 75 days.

(21) Appl. No.: 13/318,089

(22) PCT Filed: Apr. 27, 2010

(86) PCT No.: PCT/JP2010/057467
§ 371 (c)(1),
(2), (4) Date: Oct. 28, 2011

(87) PCT Pub. No.: WO2010/126045
PCT Pub. Date: Nov. 4, 2010

(65) Prior Publication Data
US 2012/0046474 A1    Feb. 23, 2012

(30) Foreign Application Priority Data
Apr. 28, 2009  (JP) .................. 2009-109634

(51) Int. Cl.
*C07D 403/06*    (2006.01)
(52) U.S. Cl.
USPC .................................................. 548/364.7
(58) Field of Classification Search
None
See application file for complete search history.

(56) References Cited

U.S. PATENT DOCUMENTS

| | | | |
|---|---|---|---|
| 5,268,486 A | 12/1993 | Waggoner et al. | |
| 5,486,616 A | 1/1996 | Waggoner et al. | |
| 5,569,766 A | 10/1996 | Waggoner et al. | |
| 5,571,388 A | 11/1996 | Patonay et al. | |
| 5,800,995 A | 9/1998 | Patonay et al. | |
| 6,294,667 B1 | 9/2001 | Jackson et al. | |
| 6,348,599 B1 | 2/2002 | Cummins et al. | |
| 6,403,807 B1 | 6/2002 | Singh et al. | |
| 2003/0113755 A1 | 6/2003 | Nishigaki et al. | |
| 2009/0069546 A1 | 3/2009 | Date et al. | |

FOREIGN PATENT DOCUMENTS

| | | |
|---|---|---|
| JP | 2003-034696 A | 2/2003 |
| JP | 2003-034697 A | 2/2003 |
| WO | 98/15829 A1 | 4/1998 |
| WO | 99/05221 A1 | 2/1999 |
| WO | 01/02374 A1 | 1/2001 |
| WO | 2007/114398 A1 | 10/2007 |

OTHER PUBLICATIONS

International Search Report of PCT/JP2010/057467, mailing date Jul. 20, 2010.
STN International HCAPLUS database, Columbus, Ohio, Accession No. 1995:83002.

*Primary Examiner* — Kamal Saeed
(74) *Attorney, Agent, or Firm* — Westerman, Hattori, Daniels & Adrian, LLP

(57) ABSTRACT

A cyanine dye derivative having high fluorescence intensity in a short wavelength region, and also a controllable migration velocity by further introducing a quaternary ammonium cation. A compound having general formula [1] or a salt thereof:

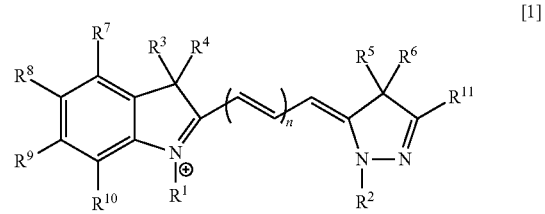

[1]

wherein $R^1$ to $R^6$ each independently represent an alkyl group having, as a substituent, a group represented by the general formula [101]:

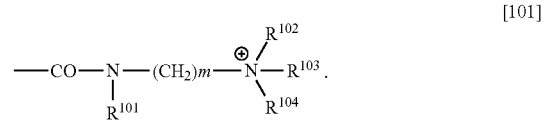

[101]

11 Claims, 2 Drawing Sheets

PYRAZOLE-BASED CYANINE DYE CONTAINING QUATERNARY AMMONIUM CATION

TECHNICAL FIELD

The present invention relates to a novel pyrazole-based cyanine dye containing a quaternary ammonium cation.

BACKGROUND ART

Recently, in a field of biochemical test and genetic test, high detection sensitivity for an analyte has been required, and positioning of a fluorescent dye as a labeling agent (a labeling substance) has become a very important factor.

Among the fluorescent dyes, cyanine dye derivatives are commonly used as a dye having a fluorescence characteristics in a near-infrared region equal to or longer than 500 nm, and, for example, Cy3, Cy5 (produced by GE Healthcare Bioscience Co., Ltd. (former name: Amersham Bioscience Co. Ltd.) and the like are known as a leading fluorescent reagent.

Cy3 and Cy5 have a structure (indolenine-based cyanine dye) where two indolenine skeletons are bound to a polymethine chain, and by using this structure as a basic skeleton, various cyanine dye derivatives have been developed aiming at, for example, improvement of water-solubility, higher sensitivity by avoiding an aggregation state or the like (see, for example, Patent Literature 1, Patent Literature 2, Patent Literature 3, or the like). In addition, as other cyanine dye derivatives, there have been developed those having a structure where an azaindolenine skeleton and a pyrazole skeleton are bound to a polymethine chain (see, for example, Patent Literature 4, Patent Literature 5, or the like). Still further, there have been developed those having a structure where two indolenine skeletons bound to, for example, a polymethine chain or the like are further cross-linked with a spacer or the like (see, for example, Patent Literature 6, Patent Literature 7, Patent Literature 8, or the like).

In addition, as a fluorescent dye exhibiting higher sensitivity and higher water-solubility at a short wavelength region than the conventional optical systems, cyanine-based dye derivatives having a pyrazole skeleton and an indole skeleton have been developed (see Patent Literature 9).

On the other hand, a fluorescent dye can also be used as an internal standard substance in an electrophoresis. However, as for a fluorescent dye which has high fluorescence intensity and also controllable migration velocity, any satisfiable dye has not been obtained and further development has been desired.

Patent Literature 1: U.S. Pat. No. 5,268,486
Patent Literature 2: U.S. Pat. No. 5,486,616
Patent Literature 3: U.S. Pat. No. 5,569,766
Patent Literature 4: JP-A-2003-034696
Patent Literature 5: JP-A-2003-034697
Patent Literature 6: U.S. Pat. No. 5,571,388
Patent Literature 7: U.S. Pat. No. 5,800,995
Patent Literature 8: WO01/02374
Patent Literature 9: WO2007/114398

SUMMARY OF INVENTION

Problem to be Solved by the Invention

The present invention has been accomplished under the above circumstances. A subject of the present invention is to provide a novel cyanine dye derivative having high fluorescence intensity in a short wavelength region, a structure where a pyrazole skeleton and an indole skeleton are bound to a polymethine chain, and also a controllable migration velocity by further introducing a quaternary ammonium cation into a molecule having said structure.

Means for Solving the Problem

The present invention provides a compound represented by the following general formula [1] or a salt thereof:

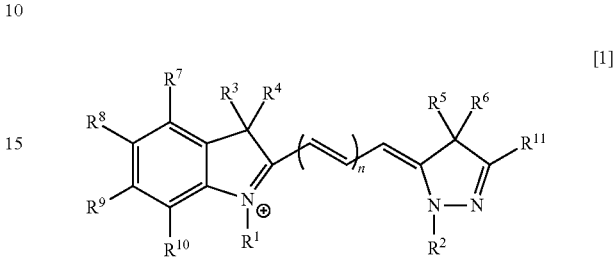

[wherein $R^1$ to $R^6$ each independently represent an alkyl group having, as a substituent, a group represented by the general formula [101]:

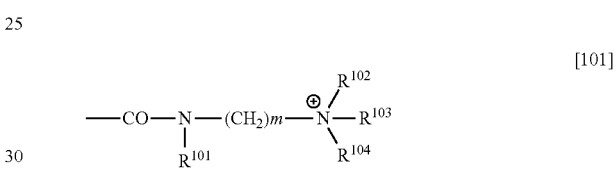

(wherein $R^{101}$ to $R^{104}$ each independently represent a hydrogen atom or an alkyl group of $C_1$ to $C_3$; m represents an integer from 2 to 6, and two or three of $R^{102}$ to $R^{104}$ together with a nitrogen atom to which they are bound may form a heterocyclic ammonium cation); or a group derived from a carboxylic acid represented by the general formula [2] which may have an amide bond:

$$—COOR^{12} \quad [2]$$

(wherein $R^{12}$ represents a hydrogen atom, an alkali metal atom, an organic ammonium ion, an ammonium ion or anion); or an alkyl group which may have, as a substituent, a group derived from a sulfonic acid represented by the general formula [3] which may have an amide bond:

$$—SO_3R^{13} \quad [3]$$

(wherein $R^{13}$ represents a hydrogen atom, an alkali metal atom, an organic ammonium ion, an ammonium ion or anion); $R^7$ to $R^{10}$ each independently represent an alkyl group, an alkynyl group, an aryl group, an alkoxy group, an aryloxy group, an alkylsulfonyl group, an arylsulfonyl group, an amino group, a group derived from a carboxylic acid represented by the general formula [2], a group derived from a sulfonic acid represented by the general formula [3], a halogen atom, a hydrogen atom, a hydroxyl group, a cyano group or a nitro group; $R^{11}$ represents a hydrogen atom, an alkyl group, an alkynyl group or an aryl group, and n represents an integer from 0 to 3, and at least one of $R^1$ to $R^6$ is an alkyl group having, as a substituent, a group represented by the general formula [101]].

Effects of the Invention

Since the pyrazole-based cyanine dye of the present invention is a novel cyanine dye derivative having a structure where a pyrazole skeleton and an indole skeleton are bound to a polymethine chain, and a quaternary ammonium cation is introduced into a molecule having said structure, the dye has a high fluorescence intensity, and is capable of controlling migration time in the case of electrophoresis by varying number of cation and anion contained in the molecule. Therefore, when the dye is used as an internal standard substance in an electrophoresis, a peak of the fluorescent substance is allowed to appear at a desired position, and hence a peak of an analyte can be clearly specified.

In addition, since the pyrazole-based cyanine dye of the present invention has a quaternary ammonium cation represented by the general formula [101], that is, said cation group has an oxygen atom or a nitrogen atom both having a lone pair, when this cation group is introduced into a fluorescent dye, the fluorescence characteristics thereof could be varied. However, it has been found that the compound of the present invention shows superior and stable fluorescence characteristics although contains said cation group.

BRIEF DESCRIPTION OF THE DRAWINGS

FIG. 1 is a drawing showing the method for preparing a DNA-labeled antibody in Example 1.
FIG. 2 is a drawing showing a layout of the capillary chip in Example 1.
FIG. 3 is a drawing schematically showing positional relationship of a sample for migration and a test solution in the capillary chip in Example 1.
FIG. 4 is an electropherogram when AFP was measured in the method of the present invention.
FIG. 5 is an electropherogram when PIVKA II was measured in the method of the present invention.

MODE FOR CARRYING OUT THE INVENTION

Figure 1:
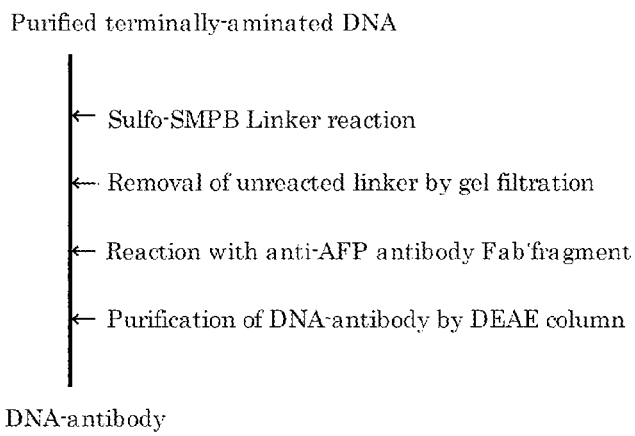
[FIG. 1]

1. Compound of the Present Invention [1]

The alkyl group of an alkyl group having, as a substituent, a group represented by the general formula [101] represented by $R^1$ to $R^6$ in the general formula [1] may be any of straight-chained, branched or cyclic one, and is preferably straight-chained one, and includes usually $C_1$ to $C_{10}$, and preferably $C_1$ to $C_6$, and more preferably $C_1$ to $C_5$. Specifically, the group includes, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a sec-hexyl group, a tert-hexyl group, a neohexyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, a sec-decyl group, a tert-decyl group, a neodecyl group, a cyclopropyl group, a cyclobutyl group, a cyclopentyl group, a cyclohexyl group, a cycloheptyl group, a cyclooctyl group, a cyclononyl group, a cyclodecyl group, and the like. Among them, for example, a straight-chained alkyl group of $C_1$ to $C_5$ such as a methyl group, an ethyl group, a n-propyl group, a n-pentyl group, and the like is preferable.

The alkyl group of $C_1$ to $C_3$ represented by $R^{101}$ to $R^{104}$ in the general formula [101] is straight-chained or branched one, preferably straight-chained one, and has usually $C_1$ to $C_3$, preferably $C_1$ to $C_2$, and more preferably $C_1$. Specifically, the group includes, for example, a methyl group, an ethyl group, a n-propyl group, an isopropyl group, and the like, and among them, a methyl group is preferable.

Among $R^{101}$ in the general formula [101], a hydrogen atom is preferable.

As $R^{101}$ to $R^{103}$, among them, a case where one is a hydrogen atom and other two are an alkyl groups (in particular, a methyl group is more preferable) is preferable.

m is an integer of usually from 2 to 6, preferably from 2 to 4, and more preferably 2.

The heterocyclic ammonium cation to be formed by 2 or 3 of $R^{102}$ to $R^{104}$ together with a nitrogen atom to which they are bound, includes, for example, a pyridinium group, and a $C_1$ to $C_3$ N-alkylpyridinium group (for example, a methylpyridinium group, an ethylpyridinium group, a N-n-propylpyridinium group, an N-isopropylpyridinium group, and the like).

The substituent in the alkyl group having, as a substituent, a group represented by the general formula [101] is preferably substituted to the terminal carbon atom of said alkyl group.

A preferable specific example of the group represented by the general formula [101] includes, for example, a dimethylammonioethylcarbamoyl group, a trimethylammonioethylcarbamoyl group, a diethylammonioethylcarbamoyl group, a triethylammonioethylcarbamoyl group, a dimethylammoniopropylcarbamoyl group, a trimethylammoniopropylcarbamoyl group, a diisopropylammoniopropylcarbamoyl group, a thisopropylammonioethylcarbamoyl group, a pyridinioethylcarbamoyl group, a pyridiniopropylcarbamoyl group, a methylpiperidinoethylcarbamoyl group, a methylpiperidinopropylcarbamoyl group, an ethylpiperidinoethylcarbamoyl group, an ethylpiperidinopropylcarbamoyl group, and the like. Among them, a dimethylammonioethylcarbamoyl group and a diethylammonioethylcarbamoyl group are preferable, further a dimethylammonioethylcarbamoyl group is more preferable.

In the general formula [1], 1 to 4, preferably 1 to 2, more preferably 1 of $R^1$ to $R^6$ are alkyl groups having, as a substituent, the group represented by the general formula [101]. Among $R^1$ to $R^6$ in the general formula [1], a group where either one of $R^1$ or $R^2$, preferably $R^1$, is an alkyl group having, as a substituent, a group represented by the general formula [101] is preferable.

In the general formula [1], the alkyl group having an amide bond of an alkyl group optionally having, as a substituent, a group derived from a carboxylic acid represented by the general formula [2] or a group derived from a sulfonic acid represented by the general formula [3], both of which may have an amide bond, represented by $R^1$ to $R^6$ includes a substituted (that is, substituted by a group derived from a carboxylic acid represented by the general formula [2] or a group derived from a sulfonic acid represented by the general formula [3]) or unsubstituted alkyl group which has usually 1 to 10 amide bonds, preferably 1 to 3 amide bonds, and more preferably one amide bond in the alkyl chain thereof.

The alkyl group of an alkyl group optionally having, as a substituent, a group derived from a carboxylic acid represented by the general formula [2] or a group derived from a sulfonic acid represented by the general formula [3], both of which may have an amide bond, represented by $R^1$ to $R^6$ may be any of straight-chained, branched or cyclic one having usually $C_1$ to $C_{10}$, preferably $C_1$ to $C_3$, and more preferably $C_1$. Specifically, the group includes, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a sec-hexyl group, a tert-hexyl group, a neohexyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, a sec-decyl group, a tert-decyl group, a neodecyl group, a cyclopropyl group, a cyclobutyl group, a cyclopentyl group, a cyclohexyl group, a cycloheptyl group, a cyclooctyl group, a cyclononyl group, a cyclodecyl group, and the like. Among them, a straight-chained alkyl group of $C_1$ to $C_5$ such as, for example, a methyl group, an ethyl group, a n-propyl group, a n-pentyl group, are preferable.

The alkyl group of an alkyl group having, as a substituent, a group derived from a carboxylic acid represented by the general formula [2] or a group derived from a sulfonic acid represented by the general formula [3], both of which may have an amide bond, represented by $R^1$ to $R^6$ includes a group where a part of hydrogen atoms in said alkyl group which may have an amide bond is substituted by said substituent (a group derived from a carboxylic acid represented by the general formula [2] or a group derived from a sulfonic acid represented by the general formula [3]). Among them, a group where said substituent is substituted at the terminal carbon atom in said alkyl group is preferable.

Among $R^1$ to $R^6$ in the general formula [1], an alkyl group having $C_1$ to $C_5$ where either one of $R^1$ or $R^2$ (preferably $R^2$), either one of $R^3$ or $R^4$, and either one of $R^5$ or $R^6$ have, as a substituent, a group derived from a sulfonic acid represented by the general formula [3] is preferable.

In the general formulas [2] and [3], the alkali metal atom represented by $R^{12}$ and $R^{13}$ includes, for example, a lithium atom, a sodium atom, a potassium atom, a rubidium atom, and the like. Among them, a sodium atom and a potassium atom are preferable, in particular, a sodium atom is more preferable.

At least one of $R^1$ to $R^6$ (preferably $R^1$) in the general formula [1] is preferably an alkyl group having, as a substituent, a group represented by the general formula [101]. Number of the group represented by the general formula [101] contained in the compound represented by the general formula [1] of the present invention is usually an integer from 1 to 6, preferably from 1 to 4, more preferably from 1 to 2, and most preferably 1.

The organic ammonium ion represented by $R^{12}$ and $R^{13}$ includes, for example, a trialkylammonium ion and the like. Said trialkylammonium ion may be any of straight-chained, branched or cyclic one having usually $C_1$ to $C_{10}$, and preferably $C_1$ to $C_6$. Specifically, the trialkylammonium ion includes, for example, a trimethylammonium ion, a triethylammonium ion, a tri-n-propylammonium ion, a triisopropylammnonium ion, a tributylammonium ion, a tripentylammonium ion, a trihexylammonium ion, a triheptylammonium ion, a trioctylammonium ion, a trinonylammonium ion, a tridecylammonium ion, a tricyclopropylammonium ion, a tricyclobutylammonium ion, a tricyclopentylammonium ion, a tricyclohexylammonium ion, a tricycloheptylammonium ion, a tricyclooctylammonium ion, a tricyclononylammonium ion, a tricyclodecylammonium ion, and the like. Among them, a trimethylammonium ion or a triethylammonium ion is preferable, in particular, a triethylammonium ion is more preferable.

In the general formula [2], the alkyl group having $C_1$ to $C_{10}$ represented by $R^{12}$ may be any of straight-chained, branched or cyclic one having usually $C_1$ to $C_{10}$, preferably $C_1$ to $C_6$, and more preferably $C_1$ to $C_3$. Specifically, the group includes, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a sec-hexyl group, a tert-hexyl group, a neohexyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, an neononyl group, a n-decyl group, an isodecyl group, a sec-decyl group, a tert-decyl group, a neodecyl group, a cyclopropyl group, a cyclobutyl group, a cyclopentyl group, a cyclohexyl group, a cycloheptyl group, a cyclooctyl group, a cyclononyl group, a cyclodecyl group, and the like.

A preferable example of the group derived from a carboxylic acid represented by the general formula [2] includes, for example, a carboxyl group (—COOH), an anion thereof [a carboxylate (—COO$^-$)], an alkali metal salt thereof (for example, a lithium salt, a sodium salt, a potassium salt, a rubidium salt, and the like), an ammonium salt thereof, an organic ammonium salt thereof (for example, a trimethylammonium salt, a triethylammonium salt, a tripropylammonium salt, and the like), and the like.

A preferable example of the group derived from a sulfonic acid represented by the general formula [3] includes, for example, a sulfo group (—SO$_3$H), an anion thereof [a sulfonate (—SO$_3^-$)], an alkali metal salt thereof (for example, a lithium salt, a sodium salt, a potassium salt, a rubidium salt, and the like), an ammonium salt thereof, an organic ammonium salt thereof (for example, a trimethylammonium salt, a triethylammonium salt, a tripropylammonium salt, and the like), and the like.

In the general formula [1], a compound where any one of $R^1$ or $R^2$ is an alkyl group of $C_1$ to $C_5$ having, as a substituent, a group derived from a carboxylic acid represented by the general formula [2] such as, for example, a carboxyethyl group, a carboxypropyl group, a carboxybutyl group, a carboxypentyl group, an anion thereof (a carboxylate), a group of alkali metal salt thereof (for example, a sodium salt, a potassium salt, and the like), a group of an organic ammonium salt thereof (for example, a trimethylammonium salt, a triethylammonium salt, an ammonium salt, and the like), and the like, or an alkyl group of $C_1$ to $C_5$ having, as a substituent, a group derived from a sulfonic acid represented by the general formula [3] such as, for example, a sulfoethyl group, a sulfopropyl group, a sulfobutyl group, a sulfopentyl group, an anion thereof (a sulfonate), a group of an alkali metal salt thereof (for example, a sodium salt, a potassium salt, and the like), a group of an organic ammonium salt thereof (for example, a trimethylammonium salt, a triethylammonium salt, an ammonium salt, and the like), and the like, and the other is an alkyl group having, as a substituent, a group represented by the general formula [101], is preferable. In particular, a case where $R^1$ is an alkyl group of $C_1$ to $C_5$ having, as a substituent, a group represented by the general formula [101], $R^2$ is an alkyl group of $C_1$ to $C_5$ having, as a substituent, a group derived from a sulfonic acid represented by the general formula [3] is more preferable.

In addition, in the general formula [1], as for a preferable combination of $R^3$ and $R^4$ and a preferable combination of $R^5$ and $R^6$, there is a case where any one thereof (that is, any one of $R^3$ or $R^4$ and any one of $R^5$ or $R^6$) is an alkyl groups of $C_1$ to $C_5$ (for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, and the like), and the others are alkyl groups of $C_1$ to $C_5$ having, as a substituent, a group derived from a carboxylic acid represented by the general formula [2] such as, for example, a carboxyethyl group, a carboxypropyl group, a carboxybutyl group, a carboxypentyl group, an anion thereof (a carboxylate), a group of alkali metal salt thereof (for example, a sodium salt, a potassium salt, and the like), a group of an ammonium salt thereof or a group of an organic ammonium salt thereof (for example, a trimethylammonium salt, a triethylammonium salt, and the like), and the like, or an alkyl groups of $C_1$ to $C_5$ having, as a substituent, a group derived from a sulfonic acid represented by the general formula [3] such as, for example, a sulfoethyl group, a sulfopropyl group, a sulfobutyl group, a sulfopentyl group, an anion thereof (a sulfonate), a group of alkali metal salt thereof (for example, a sodium salt, a potassium salt, and the like), a group of an organic ammonium salt thereof (for example, a trimethylammonium salt, a triethylammonium salt, an ammonium salt, and the like). In particular, there is a case where any one thereof (that is, any one of $R^3$ or $R^4$ and any one of $R^5$ or $R^6$) is an alkyl groups of $C_1$ to $C_5$, and the other is an alkyl group having, as a substituent, a group derived from a sulfonic acid represented by the general formula [3] is more preferable.

In the general formula [1], the alkyl group represented by $R^7$ to $R^{10}$ may be any of straight-chained, branched or cyclic one having usually $C_1$ to $C_6$, and preferably $C_1$ to $C_3$. Specifically, the group includes, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a sec-hexyl group, a tert-hexyl group, a neohexyl group, a cyclopropyl group, a cyclobutyl group, a cyclopentyl group, a cyclohexyl group, and the like.

The alkynyl group represented by $R^7$ to $R^{10}$ includes the group of usually $C_2$ to $C_6$, and preferably $C_2$ to $C_4$, and specifically includes, for example, an ethynyl group, a 2-propynyl group, a 3-butynyl group, a 1-methyl-2-propynyl group, a 4-pentynyl group, a 2-methyl-4-pentynyl group, a 5-hexynyl group, and the like.

The aryl group represented by $R^7$ to $R^{10}$ includes the group of usually $C_6$ to $C_{10}$, and specifically includes, for example, a phenyl group, a naphthyl group, and the like.

The alkoxy group represented by $R^7$ to $R^{10}$ may be any of straight-chained, branched or cyclic one having usually $C_1$ to $C_6$, and preferably $C_1$ to $C_3$. Specifically, the group includes, for example, a methoxy group, an ethoxy group, a n-propoxy group, an isopropoxy group, a n-butoxy group, an isobutoxy group, a sec-butoxy group, a tert-butoxy group, a n-pentyloxy group, an isopentyloxy group, a sec-pentyloxy group, a tert-pentyloxy group, a neopentyloxy group, a n-hexyloxy group, an isohexyloxy group, a sec-hexyloxy group, a tert-hexyloxy group, a neohexyloxy group, a cyclopropoxy group, a cyclopentyloxy group, a cyclohexyloxy group, and the like.

The aryloxy group represented by $R^7$ to $R^{10}$ is the group of usually $C_6$ to $C_{10}$, and specifically includes, for example, a phenyloxy group, a naphthoxy group, and the like.

The alkylsulfonyl group represented by $R^7$ to $R^{10}$ is the group where —OH group of the sulfo group (—$SO_3H$) is substituted by an alkyl group, and may be any of straight-chained, branched or cyclic one having usually $C_1$ to $C_6$. Specifically, the group includes, for example, a methylsulfonyl group, an ethylsulfonyl group, a n-propylsulfonyl group, an isopropylsulfonyl group, a n-butylsulfonyl group, an isobutylsulfonyl group, a sec-butylsulfonyl group, a tert-butylsulfonyl group, a n-pentylsulfonyl group, an isopentylsulfonyl group, a sec-pentylsulfonyl group, a tert-pentylsulfonyl group, a neopentylsulfonyl group, a n-hexylsulfonyl group, an isohexylsulfonyl group, a sec-hexylsulfonyl group, a tert-hexylsulfonyl group, a neohexylsulfonyl group, a cyclopropylsulfonyl group, a cyclobutylsulfonyl group, a cyclopentylsulfonyl group, a cyclohexylsulfonyl group, and the like.

The arylsulfonyl group represented by $R^7$ to $R^{10}$ is the group where —OH group of the sulfo group (—$SO_3H$) is substituted by an aryl group, and may be any of straight-chained, branched or cyclic one having usually $C_6$ to $C_{10}$. Specifically, the group includes, for example, a phenylsulfonyl group, a naphthylsulfonyl group, and the like.

The halogen atom represented by $R^7$ to $R^{10}$ includes, for example, a fluorine atom, a chlorine atom, a bromine atom, an iodine atom, and the like.

The substituted amino group represented by $R^7$ to $R^{10}$ is the group where 1 or 2 hydrogen atoms of an amino group are substituted by a substituent, and these substituent includes, for example, an alkyl group, an alkoxycarbonyl group, an acyl group, a sulfo group, and the like.

The alkyl group exemplified as a substituent of the substituted amino group represented by $R^7$ to $R^{10}$ may be any of straight-chained, branched or cyclic one having usually $C_1$ to $C_{10}$, and preferably $C_1$ to $C_6$. Specifically, the group includes, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a sec-hexyl group, a tert-hexyl group, a neohexyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, an neononyl group, a n-decyl group, an isodecyl group, a sec-decyl group, a tert-decyl group, a neodecyl group, a cyclopropyl group, a cyclobutyl group, a cyclopentyl group, a cyclohexyl group, a cycloheptyl group, a cyclooctyl group, a cyclononyl group, a cyclodecyl group, and the like.

The alkoxycarbonyl group exemplified as a substituent of the substituted amino group represented by $R^7$ to $R^{10}$ may be any of straight-chained, branched or cyclic one having usually $C_1$ to $C_{10}$, and preferably $C_1$ to $C_6$. Specifically, the group includes, for example, a methoxycarbonyl group, an ethoxycarbonyl group, a n-propoxycarbonyl group, an isopropoxycarbonyl group, a n-butoxycarbonyl group, an isobutoxycarbonyl group, a sec-butoxycarbonyl group, a tert-butoxycarbonyl group, a n-pentyloxycarbonyl group, an isopentyloxycarbonyl group, a sec-pentyloxycarbonyl group, a tert-pentyloxycarbonyl group, a neopentyloxycarbonyl group, a n-hexyloxycarbonyl group, an isohexyloxycarbonyl group, a sec-hexyloxycarbonyl group, a tert-hexyloxycarbonyl group, a neohexyloxycarbonyl group, a n-heptyloxycarbonyl group, an isoheptyloxycarbonyl group, a sec-heptyloxycarbonyl group, a tert-heptyloxycarbonyl group, a neoheptyloxycarbonyl group, a n-octyloxycarbonyl group, an isooctyloxycarbonyl group, a sec-octyloxycarbonyl group, a tert-octyloxycarbonyl group, a neooctyloxycarbonyl group, a n-nonyloxycarbonyl group, an isononyloxycarbonyl group, a sec-nonyloxycarbonyl group, a tert-nonyloxycarbonyl group, a neononyloxycarbonyl group, a n-decyloxycarbonyl group, an isodecyloxycarbonyl group, a sec-decyloxycarbonyl group, a tert-decyloxycarbonyl group, a neodecyloxycarbonyl group, a cyclopropoxycarbonyl group, a cyclobutoxycarbonyl group, a cyclopentyloxycarbonyl group, a cyclohexyloxycarbonyl group, a cycloheptyloxycarbonyl group, a cyclooctyloxycarbonyl group, a cyclononyloxycarbonyl group, a cyclodecyloxycarbonyl group, and the like.

The acyl group exemplified as a substituent of the substituted amino group represented by $R^7$ to $R^{10}$ includes, for example, a group derived from aliphatic carboxylic acid, a group derived from aromatic carboxylic acid, and the like.

Said acyl group derived from aliphatic carboxylic acid may be any of straight-chained, branched or cyclic one having usually $C_2$ to $C_{20}$, preferably $C_7$ to $C_{15}$, more preferably $C_2$ to $C_{10}$, and further more preferably $C_2$ to $C_6$, and may further have a double bond in a chain. Specifically, the group includes, for example, an acetyl group, a propionyl group, a butyryl group, an isobutyryl group, a valeryl group, an isovaleryl group, a pivaloyl group, a hexanoyl group, a heptanoyl group, an octanoyl group, a decanoyl group, a lauroyl group, a myristoyl group, a palmitoyl group, a stearoyl group, an icosanoyl group, an acryloyl group, a methacryloyl group, a crotonoyl group, an oleoyl group, and the like.

Said acyl group derived from aromatic carboxylic acid is the group having usually $C_7$ to $C_{15}$, and preferably $C_7$ to $C_{11}$, and specifically includes, for example, a benzoyl group, a naphthoyl group, an anthoyl group, and the like.

A preferable example of $R^7$ to $R^{10}$ includes a case where three of $R^7$ to $R^{10}$ are hydrogen atoms, and one of the remainder is the group derived from a sulfonic acid represented by the general formula [3]. Among said groups derived from a sulfonic acid, preferable group is, for example, a sulfo group, an anion thereof (that is, a sulfonate), an alkali metal salt thereof, an organic ammonium salt thereof, and the like, in particular, more preferable group is, for example, a sulfo group, a sulfonate, an alkali metal salt thereof (for example, a sodium salt, and the like), and a case where $R^8$ is the group derived from a sulfonic acid represented by the general formula [3] is particularly preferable.

In the general formula [1], the alkyl group represented by $R^{11}$ may be any of straight-chained, branched or cyclic one having usually $C_1$ to $C_{10}$, and preferably $C_1$ to $C_6$, more preferably $C_1$ to $C_4$. Specifically, the group includes, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a sec-hexyl group, a tert-hexyl group, a neohexyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, a isononyl group, a sec-nonyl group, a tert-nonyl group, an neononyl group, a n-decyl group, an isodecyl group, a sec-decyl group, a tert-decyl group, a neodecyl group, a cyclopropyl group, a cyclobutyl group, a cyclopentyl group, a cyclohexyl group, a cycloheptyl group, a cyclooctyl group, a cyclononyl group, a cyclodecyl group, and the like.

The alkynyl group represented by $R^{11}$ is a group having usually $C_2$ to $C_6$, and preferably $C_2$ to $C_4$, and specifically includes, for example, an ethynyl group, a 2-propinyl group, a 3-butynyl group, a 1-methyl-2-propinyl group, a 4-pentynyl group, a 2-methyl-4-pentynyl group, a 5-hexynyl group, and the like.

The aryl group represented by $R^{11}$ is a group having usually $C_6$ to $C_{10}$, and specifically includes, for example, a phenyl group, a naphthyl group, and the like.

Among $R^{11}$ in the general formula [1], preferable group is an alkyl group, in particular, more preferable group is, for example, a methyl group, an ethyl group, a n-propyl group, an isopropyl group, a n-butyl group, a n-pentyl group, a n-hexyl group, and the like.

In the general formula [1], n represents an integer of usually from 0 to 3, preferably from 1 or 2, and more preferably 2.

As for the group (for example, a sulfo group, and the like) derived from a sulfonic acid represented by the general formula [3] to be contained in the compound of the present invention in the general formula [1], it is preferable that more groups are introduced because the group improves water-solubility, inhibits fluorescence quenching due to aggregation among said dye molecules, and increases fluorescence intensity. The group is contained in the compound of the present invention in an amount of usually 1 to 4, preferably 3 to 4, and more preferably 4. In addition, when 4 groups derived from a sulfonic acid represented by the general formula [3] in the compound of the present application are contained, preferable location to be introduced is as follows. That is, the group is preferably introduced at either $R^3$ or $R^4$ in the general formula [1], either $R^5$ or $R^6$, and either $R^1$ or $R^2$ (preferably $R^2$) as an alkyl group of $C_1$ to $C_5$ having, as a substituent, a group derived from a sulfonic acid represented by the general formula [3], and further at $R^8$ as a group derived from a sulfonic acid represented by the general formula [3].

The compound represented by the general formula [1] includes, for example, a compound represented by the general formula [1-1]:

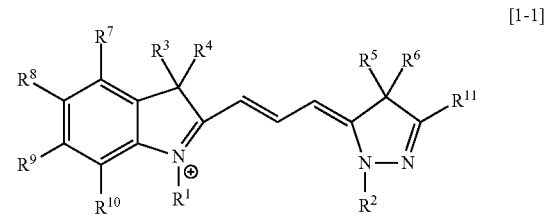

[1-1]

(wherein $R^1$ to $R^{11}$ are the same as above) (corresponding to the case where it is n=1 in the general formula [1]); a compound represented by the general formula [1-2]:

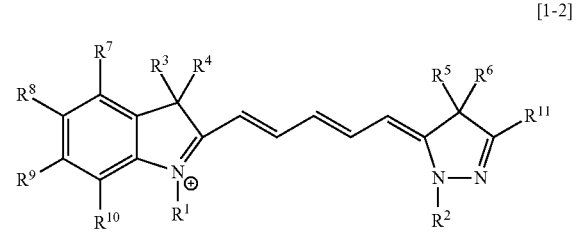

[1-2]

(wherein $R^1$ to $R^{11}$ are the same as above) (corresponding to the case where it is n=2 in the general formula [1]); a compound represented by the general formula [1-3]:

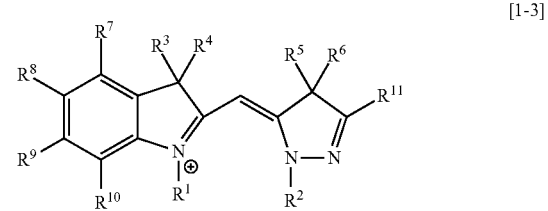

[1-3]

(wherein $R^1$ to $R^{11}$ are the same as above) (corresponding to the case where it is n=0 in the general formula [1]); and a compound represented by the general formula [1-4]:

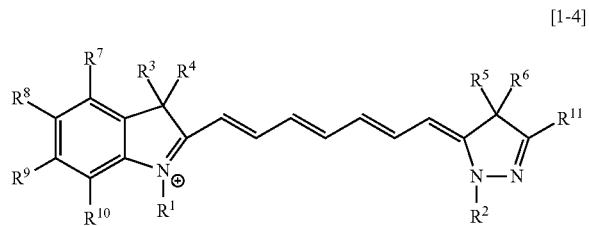

[1-4]

(wherein $R^1$ to $R^{11}$ are the same as above) (corresponding to the case where it is n=3 in the general formula [1]), and among them, the compound represented by the general formula [1-1] or [1-2] is preferable.

In addition, among the compounds [1] of the present invention, for example, a compound represented by the following general formula [1']:

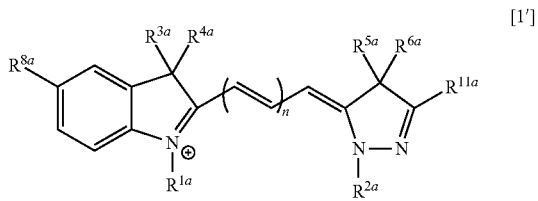

[1']

(wherein $R^{1a}$ to $R^{6a}$ each independently represent an alkyl group having, as a substituent, a group represented by the general formula [101], or an alkyl group optionally having, as a substituent, a group derived from a carboxylic acid represented by the general formula [2] or a group derived from a sulfonic acid represented by the general formula [3]; $R^{8a}$ represents a group derived from a sulfonic acid represented by the general formula [3]; $R^{11a}$ represents an alkyl group; and n is the same as above; and at least one of $R^{1a}$ to $R^{6a}$ represents an alkyl group having, as a substituent, a group represented by the general formula [101]) is preferable.

In the general formula [1'], the alkyl group having, as a substituent, a group represented by the general formula [101] represented by $R^{1a}$ to $R^{6a}$ includes same groups as exemplified for the alkyl group having, as a substituent, a group represented by the general formula [101] represented by $R^1$ to $R^6$ in the aforementioned general formula [1].

The alkyl group optionally having, as a substituent, a group derived from a carboxylic acid represented by the general formula [2] represented by $R^{1a}$ to $R^{6a}$ or a group derived from a sulfonic acid represented by the general formula [3] includes the same groups as exemplified for the alkyl group optionally having, as a substituent, a group derived from a carboxylic acid represented by the general formula [2] or a group derived from a sulfonic acid represented by the general formula [3] of the alkyl group optionally having, as a substituent, a group derived from a carboxylic acid represented by the general formula [2] or a group derived from a sulfonic acid represented by the general formula [3] both of which may have an amide bond, represented by $R^1$ to $R^6$ in the aforementioned general formula [1].

$R^{3a}$ and $R^{4a}$ each independently include an alkyl group optionally having as a substituent a group derived from a carboxylic acid represented by the general formula [2] or a group derived from a sulfonic acid represented by the general formula [3]. Among these groups, a case where either one is an alkyl group having as a substituent a group derived from a carboxylic acid represented by the general formula [2] or a group derived from a sulfonic acid represented by the general formula [3], and the other is an alkyl group is preferable.

$R^{5a}$ and $R^6$ each independently represent an alkyl group optionally having as a substituent a group derived from a carboxylic acid represented by the general formula [2] or a group derived from a sulfonic acid represented by the general formula [3]. Among these groups, a case where either one is an alkyl group having as a substituent a group derived from a carboxylic acid represented by the general formula [2] or a group derived from a sulfonic acid represented by the general formula [3], and the other is an alkyl group is preferable.

The alkyl group represented by $R^{11a}$ includes the same groups as exemplified for the alkyl group represented by $R^{11}$ in the aforementioned general formula [1].

In the general formula [1'], at least one of $R^{1a}$ to $R^{6a}$ is an alkyl group having as a substituent a group represented by the general formula [101].

Preferable specific examples of the compound represented by the general formula [1-2] include, for example, those shown in the following Table 1, and the like.

TABLE 1

|   | $R^1$ | $R^2$ | $R^3$ | $R^4$ | $R^5$ |
|---|---|---|---|---|---|
| 1-2-1 | —(CH$_2$)$_5$CONH(CH$_2$)$_2$NH(CH$_3$)$_2$$^+$ | —(CH$_2$)$_3$SO$_3$$^-$ | —CH$_3$ | —(CH$_2$)$_3$SO$_3$Na | —CH$_3$ |
| 1-2-2 | —(CH$_2$)$_5$CONH(CH$_2$)$_2$NH(CH$_3$)$_2$$^+$ | —(CH$_2$)$_3$SO$_3$H | —CH$_3$ | —(CH$_2$)$_3$SO$_3$Na | —CH$_3$ |
| 1-2-3 | —(CH$_2$)$_5$CONH(CH$_2$)$_2$NH(CH$_3$)$_2$$^+$ | —(CH$_2$)$_3$SO$_3$$^-$ | —CH$_3$ | —(CH$_2$)$_3$SO$_3$Na | —CH$_3$ |
| 1-2-4 | —(CH$_2$)$_2$CONH(CH$_2$)$_2$NH(CH$_3$)$_2$$^+$ | —(CH$_2$)$_2$COO$^-$ | —CH$_3$ | —CH$_3$ | —CH$_3$ |
| 1-2-5 | —(CH$_2$)$_2$CONH(CH$_2$)$_2$NH(CH$_3$)$_2$$^+$ | —(CH$_2$)$_3$SO$_3$H | —CH$_3$ | —CH$_3$ | —CH$_3$ |
| 1-2-6 | —(CH$_2$)$_5$CONH(CH$_2$)$_2$NH(CH$_3$)$_2$$^+$ | —(CH$_2$)$_3$SO$_3$H | —CH$_3$ | —CH$_3$ | —CH$_3$ |

|   | $R^6$ | $R^7$ | $R^8$ | $R^9$ | $R^{10}$ | $R^{11}$ |
|---|---|---|---|---|---|---|
| 1-2-1 | —(CH$_2$)$_2$COOH | H | —SO$_3$Na | H | H | —CH$_3$ |
| 1-2-2 | —(CH$_2$)$_2$COOC$_2$H$_5$ | H | —SO$_3$Na | H | H | —CH$_3$ |
| 1-2-3 | —(CH$_2$)$_3$SO$_3$Na | H | —SO$_3$Na | H | H | —CH$_3$ |
| 1-2-4 | —(CH$_2$)$_3$SO$_3$Na | H | —SO$_3$Na | H | H | —CH$_3$ |
| 1-2-5 | —(CH$_2$)$_2$COOH | H | —SO$_3$Na | H | H | —CH$_3$ |
| 1-2-6 | —CH$_3$ | H | —SO$_3$Na | H | H | —CH$_3$ |

2. Method for Synthesizing Compound [1] of the Present Invention 2-1. Synthesis of an Indolenine Compound-Pyrazole Compound Complex (Corresponding to the Compound Represented by the General Formula [1] of the Present Invention)

The compound represented by the general formula [1] may be synthesized, for example, by the following method:

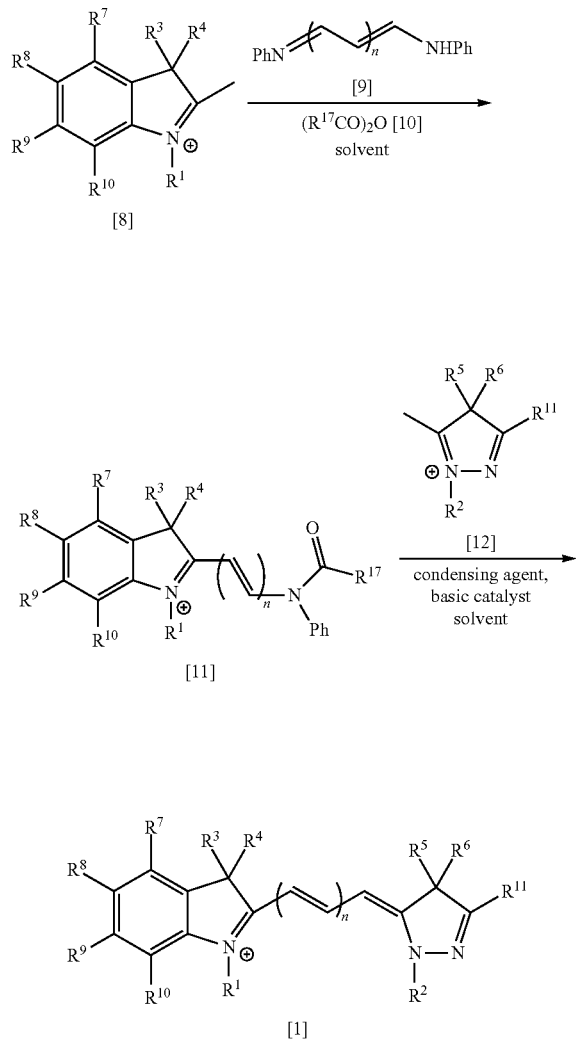

*Ph = phenyl group (wherein $R^{17}$ represents an alkyl group or an aryl group, and $R^1$ to $R^{11}$ and n are the same as above).

In the general formulas [10] and [11], the alkyl group represented by $R^{17}$ may be any of straight-chained, branched or cyclic one having $C_1$ to $C_{10}$, and preferably $C_1$ to $C_3$. Specifically, the group includes, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a sec-hexyl group, a tert-hexyl group, a neohexyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, a sec-decyl group, a tert-decyl group, a neodecyl group, a cyclopropyl group, a cyclobutyl group, a cyclopentyl group, a cyclohexyl group, a cycloheptyl group, a cyclooctyl group, a cyclononyl group, a cyclodecyl group, and the like.

The aryl group represented by $R^{17}$ includes a group of usually $C_6$ to $C_{10}$, and specifically includes, for example, a phenyl group, a naphthyl group, and the like.

That is, firstly, an indolenine compound represented by the general formula [8] (an indolenine skeleton moiety), a compound represented by the general formula [9] [1 to 2 times in molar amount to the compound represented by the general formula [8]] and an acid anhydride represented by the general formula [10] [1 to 20 times in molar amount to the compound represented by the general formula [8]] (for example, acetic anhydride, propionic anhydride, butyric anhydride, benzoic anhydride, and the like) are dissolved in a solvent (carboxylic acids such as, for example, acetic acid, propionic acid, butylic acid, and the like, nitriles such as, for example, acetonitrile, propionitrile, n-butyronitrile, and the like) if necessary, and reacted at 0 to 150° C. (preferably 40 to 120° C.) for 0.1 to 24 hours (preferably 0.5 to 12 hours, and more preferably 1 to 8 hours) to obtain a compound represented by the general formula [11].

Subsequently, the compound represented by the general formula [11] and a compound represented by the general formula [12] (a pyrazole skeleton moiety) [0.5 to 10 times, preferably 1 to 5 times in molar amount to the compound represented by the general formula [11]] are reacted in the presence of a basic catalyst (organic amines such as, for example, pyridine, triethylamine, N,N-dimethylaniline, piperidine, 4-dimethylaminopyridine, 1,5-diazabicyclo[4.3.0]nona-5-ene, 1,8-diazabicyclo[5.4.0]undeca-7-ene, tri-n-butylamine, and the like; metal hydrides such as, for example, sodium hydride, and the like; basic alkali metal compounds such as, for example, n-butyllithium, and the like), using a dehydration condensation agent [inorganic dehydration agents such as, for example, concentrated sulfuric acid, phosphorus pentoxide, anhydrous zinc chloride; carbodiimides such as, for example, dicyclohexylcarbodiimide, diisopropylcarbodiimide, 1-ethyl-3-(3-dimethylaminopropylcarbodiimide) hydrochloride; acetic anhydride; polyphosphoric acid; carbonyldiimidazole; p-toluenesulfonyl chloride; and the like], and if necessary in a solvent (amides such as, for example, N,N-dimethylformamide (DMF), N,N-dimethylacetamide (DMA), acetamide, N-methylpyrolidone; nitriles such as, for example, acetonitrile, propionitrile, n-butyronitrile; alcohols such as, for example, methanol, ethanol, propanol, isopropanol, butanol, ethylene glycol, 1,4-butandiol; ethers such as, for example, tetrahydrofuran, dioxane, anisole, ethylene glycol monoethyl ether; sulfoxides such as, for example, dimethylsulfoxide) at 0 to 150° C. (preferably 40 to 120° C.) for 0.1 to 24 hours (preferably 0.5 to 12 hours, and more preferably 1 to 8 hours), to obtain the desired compound represented by the general formula [1].

2-2. Cation-Introducing Step

A method for introducing the group represented by the general formula [101] relevant to the present invention will be explained taking for example a case where a compound represented by the general formula [24] [that is, a compound corresponding to a case where $R^1$ is an alkyl group having as a substituent a group represented by the general formula

[101] in the general formula [1] wherein $R^{104}$ is a hydrogen atom], among the compounds represented by the general formula [1] is synthesized:

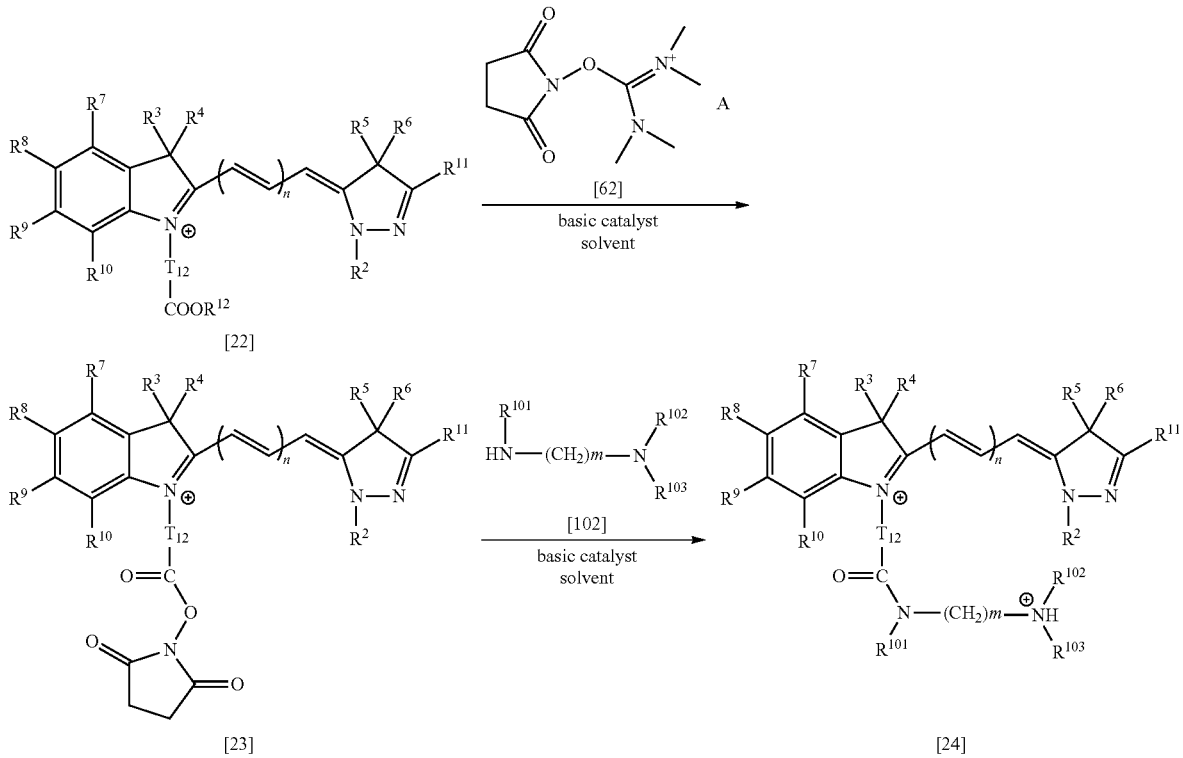

(wherein $T_{12}$ represents an alkylene group, A represents a tetrafluoroborate or a hexafluorophosphate, and $R^3$ to $R^{12}$, $R^{101}$ to $R^{103}$, m and n are the same as above).

It should be noted that the compound represented by the general formula [22] corresponds to a compound where $R^1$ is an alkyl group having as a substituent a group derived from a carboxylic acid represented by the general formula [2] (that is, a group corresponding to -$T_{12}$-$COOR^{12}$ group) among the compounds represented by the general formula [1].

In the general formulas [22] to [24], the alkylene group represented by $T_{12}$ may be any of straight-chained or branched one, and is preferably straight-chained one. The group has usually $C_1$ to $C_6$, and preferably $C_1$ to $C_4$, and specifically includes a straight-chained alkylene group such as, for example, a methylene group, an ethylene group, a trimethylene group, a tetramethylene group, a pentamethylene group, a hexamethylene group; a branched alkylene group such as an ethylidene group, a propylidene group, an isopropylidene group, an ethylethylene group, a 1,2-dimethylethylene group, a 1,2-diethylethylene group, a 1,2-di-n-propylethylene group, a 1,2-di-n-butylethylene group; and the like, and among them, a straight-chained alkylene group is preferable, in particular, an ethylene group, a pentamethylene group and the like are more preferable.

That is, a compound represented by the general formula [22] is reacted with a succinimidization reagent such as, for example, a compound represented by the general formula [62] (1 to 10 times in molar amount to the compound represented by the general formula [22]) in the presence of a basic catalyst (organic amines such as, for example, N-ethyldiisopropylamine, pyridine, triethylamine, N,N-dimethylaniline, piperidine, 4-dimethylaminopyridine, 1,5-diazabicyclo[4.3.0]non-5-ene, 1,8-diazabicylo[5.4.0]undec-7-ene, tri-n-butylamine) in an appropriate solvent (amides such as, for example, DMF, DMA, acetamide, N-methylpyrolidone) at 0 to 40° C. for 0.1 to 12 hours, to obtain a compound represented by the general formula [23].

Subsequently, the compound represented by the general formula [23] is reacted with a canonization reagent, for example, represented by the general formula [102] (1 to 5 times in molar amount to the compound represented by the general formula [23]) in an appropriate solvent (amides such as, for example, DMF, DMA, acetamide, N-methylpyrolidone) at 0 to 40° C. for 0.1 to 12 hours, to obtain a compound represented by the general formula [24].

The succinimidation reagent relevant to the present invention includes not only the compound represented by the general formula [62] but also all of those to be usually used in this field, and specifically, for example, di(N-succinimidyl)carbonate (DSC), 2-succinimide-1,1,3,3-tetramethyluronium tetrafluoroborate (TSTU), 2-(5-norbornene-2,3-dicarboxylmide)-1,1,3,3-tetramethyluronium tetrafluoroborate (TNTU), and the like. In addition, when succinimidation reaction is carried out, the reaction may be carried out in the presence of an appropriate basic catalyst (organic amines such as, for example, triethylamine, N-ethyldiisopropylamine, pyridine, N,N-dimethylaniline, piperidine, 4-dimethylaminopyridine, 1,5-diazabicyclo[4.3.0]non-5-ene, 1,8-diazabicylo[5.4.0]undec-7-ene, tri-n-butylamine, and the like).

2-3. Synthesis of Indolenine Compound

A method for synthesizing a compound represented by the general formula [8] (an indolenine skeleton moiety) will be explained below:

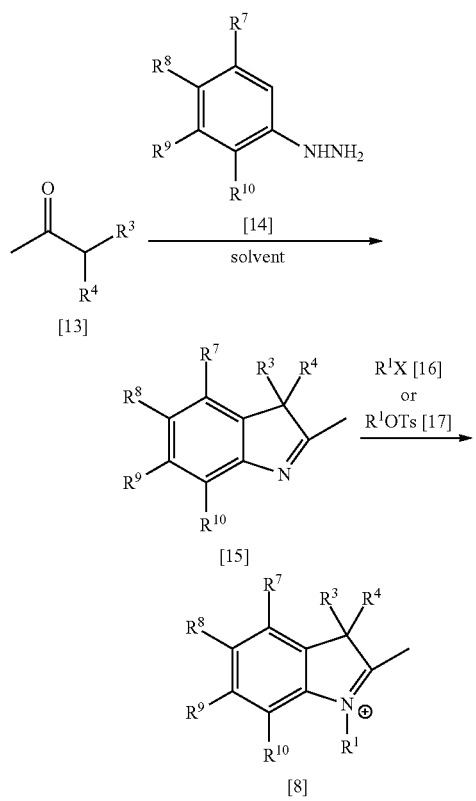

*TS = Tosyl(p-toluenesulfonyl) group (wherein X represents a halogen atom, $R^1$, $R^3$, $R^4$ and $R^7$ to $R^{10}$ are the same as above).

In the general formula [16], the halogen atom represented by X includes, for example, a fluorine atom, a chlorine atom, a bromine atom, an iodine atom, and the like.

That is, a ketone compound represented by the general formula [13] and a compound represented by the general formula [14] are reacted in an appropriate solvent (carboxylic acids such as, for example, acetic acid, propionic acid; alcohols such as, for example, ethylene glycol, 1,4-butanediol; and the like) at 40 to 250° C. for 0.1 to 24 hours, to obtain a compound represented by the general formula [21] (see, for example, Journal of Organic Chemistry, 42(14), 2474-80, 1977, etc.).

Subsequently, a compound represented by the general formula [15] and a halide represented by the general formula [16] or a tosylate compound represented by the general formula [17] are dissolved in an appropriate solvent (halogenated aromatic hydrocarbons such as, for example, chlorobenzene, 1,2-dichlorobenzene; halogenated hydrocarbons such as, for example, 1,2-dichloroethane; aromatic hydrocarbons such as, for example, toluene, xylene, benzene; amides such as, for example, DMF, DMA, acetamide, N-methylpyrolidone; and the like), and the solution is reacted at 40 to 200° C. for 1 to 24 hours, to obtain a compound represented by the general formula [8] (see, for example, J. Chem. Soc., Perkin Trans. 1, 947-952, 1984, etc.).

The ketone compound represented by the general formula [13] may use a commercial product (for example, 3-methyl-2-butanone, 3-methyl-2-pentanone, 3-methyl-2-hexanone, 1-cyclopropylethanone, 1-cyclobutylethanone, and the like), or one synthesized as appropriate by a usual method. An example of synthesis of said ketone compound includes, for example, a method where ethyl 2-methylacetoacetate is reacted with a compound having a leaving group (for example, a halogen atom, a tosylate group, and the like) in the presence of a basic catalyst (metal hydrides such as, for example, sodium hydride, potassium hydride; alkali metal carbonate such as, for example, lithium carbonate, sodium carbonate, potassium carbonate; alkali metal alkoxides such as, for example, sodium methoxide, sodium ethoxide, potassium tert-butoxide; basic alkali metal compounds such as, for example, n-butyllithium; alkali metal amides such as, for example, lithium diisopropylamide; and the like) in an appropriate solvent (amides such as, for example, DMF, DMA, acetamide, N-methylpyrolidone; alcohols such as, for example, methanol, ethanol, propanol, isopropanol, butanol, ethylene glycol; ethers such as, for example, tetrahydrofuran, dioxane, ethylene glycol monoethyl ether; sulfoxides such as, for example, dimethylsulfoxide; and the like) at −80 to 100° C. for 0.1 to 24 hours, subsequently the resultant solution is subjected to decarboxylation using an acid catalyst (see, for example, Modern Synthetic Reactions, California, 2'nd ed., P. 492, 510 and 756 (1972)), and the like.

The compound represented by the general formula [14] may use a commercial product, or one synthesized as appropriate by a usual method.

2-4. Synthesis of a Pyrazole Compound

A method for synthesizing the compound represented by the general formula [12] (a pyrazole skeleton moiety) will be explained below:

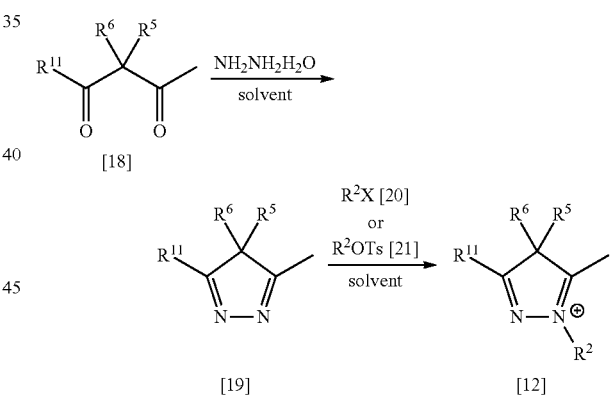

(wherein $R^2$, $R^5$ to $R^6$, $R^{11}$ and X are the same as above).

That is, a diketone compound represented by the general formula [18] and hydrazine are subjected to dehydration reaction in an appropriate solvent (alcohols such as, for example, methanol, ethanol, propanol, isopropanol, butanol, ethylene glycol, and the like) at 60 to 100° C. for 1 to 4 hours, to obtain a 4H-pyrazole compound represented by the general formula [19] (see, for example, Adv. Heterocycle. Chem. Vol. 34, 53-78, 1983, etc.).

Subsequently, the 4H-pyrazole compound represented by the general formula [19] and a halide represented by the general formula [20] or a tosylate compound represented by the general formula [21] is subjected to N-alkylation reaction in an appropriate solvent (halogenated aromatic hydrocarbons such as, for example, chlorobenzene, 1,2-dichlorobenzene; halogenated hydrocarbons such as, for example, 1,2-dichloroethane; aromatic hydrocarbons such as, for example, toluene, xylene, benzene; amides such as, for example, DMF, DMA, acetamide, N-methylpyrolidone; and the like) at 80 to 140° C. for 1 to 12 hours, to obtain a compound represented by the general formula [12] (see, for example, J. Chem. Soc., Perkin Trans. 1, 947-952, 1984, etc.).

The diketone compound represented by the general formula [18] may use a commercial product (for example, 3,3-dimethyl-2,4-pentan-dione, and the like), or one synthesized as appropriate by a usual method. An example of the synthesis of said diketone compound includes, for example, a method where 3-methyl-2,4-pentandione or ethyl 4-acetyl-5-oxohexanoate ester is reacted with a compound having a leaving group (for example, a halogen atom, a tosylate group, and the like) in the presence of a basic catalyst (metal hydrides such as, for example, sodium hydride, potassium hydride; alkali metal carbonates such as, for example, lithium carbonate, sodium carbonate, potassium carbonate; alkali metal alkoxides such as, for example, sodium methoxide, sodium ethoxide, potassium tert-butoxide; basic alkali metal compounds such as, for example, n-butyl lithium; alkali metal amides such as, for example, lithium diisopropylamide; and the like) in an appropriate solvent (amides such as, for example, DMF, DMA, acetamide, N-methylpyrolidone; alcohols such as, for example, methanol, ethanol, propanol, isopropanol, butanol, ethylene glycol; ethers such as, for example, tetrahydrofuran, dioxane, ethylene glycol monoethyl ether; sulfoxides such as, for example, dimethylsulfoxide; and the like) at –80 to 100° C. for 0.1 to 24 hours (see, for example, Modern Synthetic Reactions, California, 2'nd ed., p. 492, 510; 756 (1972), etc.), and the like.

3. Properties of Compound of the Present Invention [1]

The thus obtained compound [1] of the present invention is a fluorescent substance having an maximum excitation wavelength at around 635 nm, and uses such as, for example, fluorescent labeling substance, internal standard substance in electrophoresis are expected.

Since compound [1] of the present invention has a group represented by the general formula [101] (that is, an ammonium cation group) in a molecule thereof, when the compound is subjected to an electrophoresis from plus side to minus side, migration time can be delayed by the presence of the ammonium cation relevant to the present invention. Further, since it is possible to introduce a group derived from a carboxylic acid represented by the general formula [2] or a group derived from a sulfonic acid represented by the general formula [3] as an anion group in the compound of the present invention, it becomes possible to synthesize the compound of the present invention which has a controlled mobility in an electrophoresis.

In particular, when compound [1] of the present invention is used as an internal standard substance together with a compound which has the same basic skeleton as compound [1] of the present invention and in which the group represented by the general formula [101] relevant to the present invention is substituted by a group derived from a carboxylic acid represented by the general formula [2] or a group derived from a sulfonic acid represented by the general formula [3] (that is, an anion group) (hereinafter, referred to as an anion-group-containing compound relevant to the present invention), it becomes possible to shorten the migration time of the anion-group-containing compound relevant to the present invention than that of compound [1] relevant to the present invention in the electrophoresis from plus side to minus side, thereby to adjust the peaks of two internal standard substances so that a peak of an analyte is positioned between the peaks of two internal standard substances. By this method, it becomes possible to identify a peak of the analyte easily.

Specific example of the anion-group-containing compound relevant to the present invention includes, for example, a compound represented by the general formula [50] or a salt thereof:

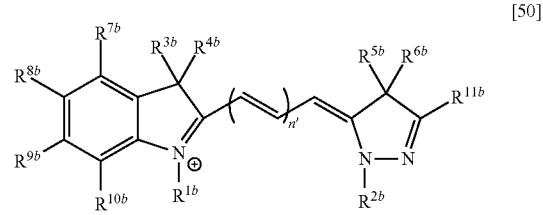

[50]

[wherein $R^{1b}$ to $R^{6b}$ each independently represent an alkyl group optionally having, as a substituent, a group derived from a carboxylic acid represented by the general formula [2] which may have an amide bond:

—COOR$^{12}$ [2]

(wherein $R^{12}$ is the same as above), or a group derived from a sulfonic acid represented by the general formula [3] which may have an amide bond:

—SO$_3$R$^{13}$ [3]

(wherein $R^{13}$ is the same as above), $R^{7b}$ to $R^{10b}$ each independently represent an alkyl group, an alkynyl group, an aryl group, an alkoxy group, an aryloxy group, an alkylsulfonyl group, an aryl sulfonyl group, a substituted amino group, a group derived from a carboxylic acid represented by the general formula [2], a group derived from a sulfonic acid represented by the general formula [3], a halogen atom, a hydrogen atom, a hydroxyl group, a cyano group or a nitro group, $R^{11b}$ represents a hydrogen atom, an alkyl group, an alkynyl group or an aryl group, and n' represents an integer from 0 to 3, and at least one of $R^{1b}$ to $R^{6b}$ is a group derived from a carboxylic acid represented by the general formula [2] or a group derived from a sulfonic acid represented by the general formula [3], or has these groups as a substituent]. The above-described compound represented by the general formula [50] or a salt thereof is a fluorescent substance having an excitation wavelength at around 635 nm, and can be a useful internal standard substance in a measurement by fluorescence detection.

The alkyl group optionally having as a substituent a group derived from a carboxylic acid represented by the general formula [2] or a group derived from a sulfonic acid represented by the general formula [3] both of which may have an amide bond represented by $R^{1b}$ to $R^{6b}$ in the general formula [50] includes the same groups as exemplified for the alkyl group optionally having as a substituent a group derived from a carboxylic acid represented by the general formula [2] or a group derived from a sulfonic acid represented by the general formula [3] both of which may have an amide bond represented by $R^1$ to $R^6$ in the general formula [1].

The alkyl group having as a substituent a group derived from a carboxylic acid represented by the general formula [2] or a group derived from a sulfonic acid represented by the general formula [3] both of which may have an amide bond represented by $R^{1b}$ to $R^{6b}$ includes the one where a part of hydrogen atoms in said alkyl group optionally having an amide bond is substituted by said substituent (a group derived from a carboxylic acid represented by the general formula [2] or a group derived from a sulfonic acid represented by the general formula [3]), and among them, a group where said substituent is substituted at the terminal carbon atom of said alkyl group is preferable.

The alkyl group, the alkynyl group, the aryl group, the alkoxy group, the aryloxy group, the alkylsulfonyl group, the arylsulfonyl group, the halogen atom and the substituted amino group represented by $R^{7b}$ to $R^{10b}$ include the same as those exemplified for the alkyl group, the alkynyl group, the aryl group, the alkoxy group, the aryloxy group, the alkylsulfonyl group, the arylsulfonyl group, the halogen atom and the substituted amino group represented by $R^7$ to $R^{10}$ in the general formula [1], respectively.

The alkyl group, the alkynyl group and the aryl group represented by $R^{11b}$ in the general formula [50] include the same as those exemplified for the alkyl group, the alkynyl group and the aryl group represented by $R^{11}$ in the general formula [1], respectively.

Among $R^{11b}$, an alkyl group is preferable, in particular, for example, a methyl group, an ethyl group, an n-propyl group, an isopropyl group, a n-butyl group, a n-pentyl group, a n-hexyl group, and the like are more preferable.

In the general formula [50], n' represents an integer usually from 0 to 3, preferably 1 or 2, and more preferably 2.

Preferable specific example of the general formula [50] includes, for example, the following compounds:

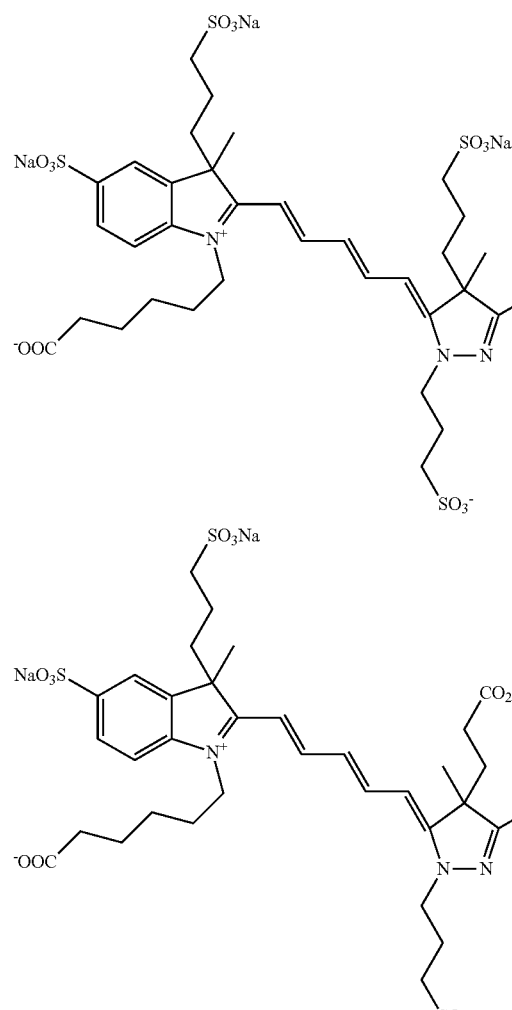

R' = Et or ⊖

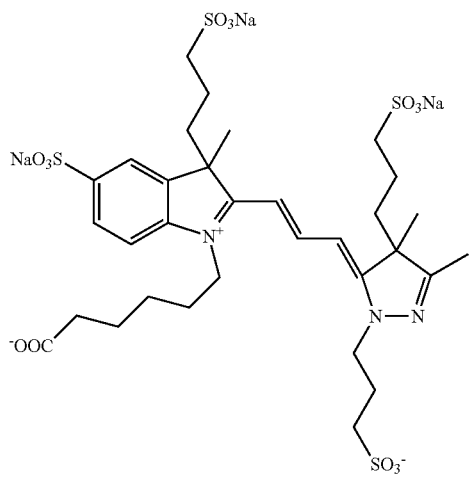

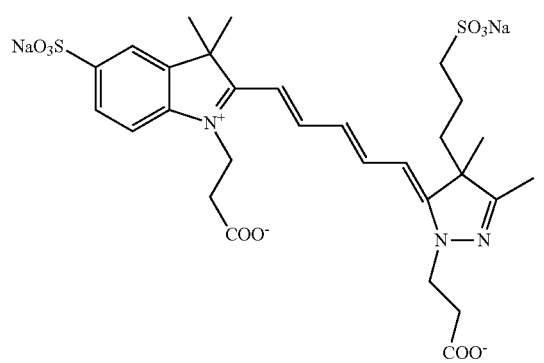

R = Et or ⊖

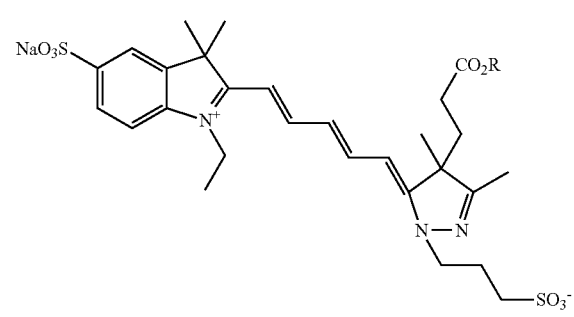

R = Et or ⊖ and among them, the following compound:

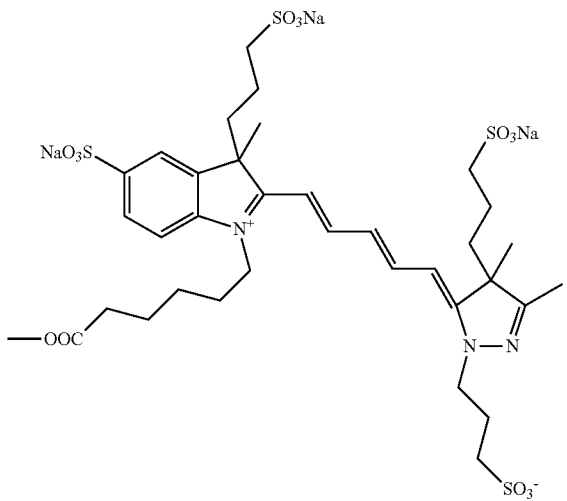

is preferable.

The compound represented by the general formula [50] which is the anion-group-containing compound relevant to the present invention can be synthesized, for example, according to the common method (WO 2007/114398).

Analyte in which the compound of the present invention can be used as an internal standard substance or a fluorescent labeling substance is not particularly limited but includes all of measurement substances in this field. Specifically, the analyte includes, for example, peptide chain (for example, C-peptide, angiotensin 1, and the like), protein [serum protein such as, for example, immunoglobulin A (IgA), immunoglobulin E (IgE), immunoglobulin G (IgG), immunoglobulin M (IgM), immunoglobulin D (IgD), β2-microglobulin, albumin, degradation product thereof, ferritin; enzyme protein such as, for example, amylase, alkaline phosphatase, γ-glutamyltransferase; protein, peptide or sugar chain derived from bacterium such as, for example, tuberculosis bacterium, pneumococcus, diphtheria bacillus, meningococcus, gonococcus, staphylococcus, streptococcus, intestinal bacterium, coli bacterium, *Helicobacter pylori*; virus such as, for example, rubella virus, herpes virus, hepatitis virus, ATL virus, AIDS virus, influenza virus, adenovirus, enterovirus, poliovirus, EB virus, HAV, HBV, HCV, HIV, HTLV; fungus such as, for example, *candida, cryptococcus*; spirochete such as *leptospira, pallidum Treponema*; microorganisms such as *chlamydia, mycoplasma*; various kinds of allergens causing allergy such as bronchial asthma, allergic rhinitis, atopic dermatitis such as allergens derived from, for example, house dust; mites such as, for example, *dermatophagoides* and *farina, dermatophagoides pteronyssinus*; pollen of, for example, Japanese cedar, Japanese cypress. *Paspalum thunbergii* Kunth, blackweed, timothy grass, vernal grass, rye; animals such as, for example, cat, dog, crab; foods such as, for example, rice, egg white; fungus, insect, wood, medical agent, chemical substance, and the like; lipid such as, for example, lipoprotein; protease such as, for example, trypsin, plasmin, serine protease; tumor marker protein such as, for example, AFP, PSA, CEA, PG I, PG II; and the like], sugar chain (tumor marker sugar chain antigen sugar chain such as, for example, CA 19-9, PIVKA-II, CA 125, sugar chain possessed by a substance having a particular sugar chain produced by cancer cell; for example, ABO sugar chain, and the like), lectin (for example, concanavalin A, lentils lectin, marrow bean lectin, angel trumpet lectin, wheat germ lectin, and the like), phospholipid (for example, cardiolipin, and the like), lipopolysaccharide (for example, endotoxin, and the like), chemical substance (hormone such as, for example, PTH, T3, T4, TSH, insulin, LH, FSH, prolactin; endocrine disrupters such as, for example, tributyltin, nonylphenol, 4-octylphenol, di-n-butyl phthalate, dicyclohexyl phthalate, benzophenone, octachlorostyrene, di-2-ethylhexyl phthalate), receptor (for example, receptor for estrogen, TSH, and the like), ligand (for example, estrogen, TSH, and the like), and among them, tumor marker protein such as, for example, AFP, PSA, CEA, PG I, PG II, and tumor marker sugar chain antigen sugar chain such as, for example, CA 19-9, PIVKA-II, CA 125, sugar chain possessed by a substance having a particular sugar chain produced by cancer cell, are preferable, and AFP and PIVKA-II are particularly preferable.

Electrophoresis method in the measurement method using the compound of the present invention as an internal standard substance or a fluorescent labeling substance includes all of the methods usually used in this field, and among them, electrophoresis method carried out in a capillary (capillary electrophoresis method) is preferable. Among said capillary electrophoresis methods, electrophoresis method carried out in a capillary chip is preferable. The capillary (micro) chip electrophoresis method is a technology where a capillary having a cross-section of 100 μm or less in diameter is formed on a substrate of a chip and electrophoresis is carried out in this capillary, and a method by which substances present in a sample are separated utilizing a difference in charge as a difference in mobility by applying electric voltage to inside of the capillary.

The capillary electrophoresis method can be classified into capillary zone electrophoresis method and capillary gel electrophoresis method depending on a migration solution to be used, and the method of the present invention can be applied to both of them. Among the above methods, capillary gel electrophoresis method is preferable in view of accuracy of separation.

Material of the capillary to be used for the above-described capillary electrophoresis method is not particularly limited, and any material commonly used in this field may be used. Specifically, the material includes, for example, silica-based compound such as, for example, glass, quartz, silicon; synthetic polymer such as, for example, cyclic olefin copolymer (COC), cyclic olefin polymer (COP), polymethyl methacrylate, polymethyl siloxane, polyvinyl chloride, polyurethane, polystyrene, polysulfon, polycarbonate, polytetrafluoroethylene; and the like, and among them, synthetic polymer is preferable. In addition, internal diameter and length of the capillary are not particularly limited so long as analyte can be separated, but internal diameter is usually 1 to 1000 μm, preferably 1 to 200 μm, and more preferably 1 to 100 μm. Length is usually 0.1 mm to 100 cm, preferably 0.1 mm to 20 cm, and more preferably 0.1 mm to 10 cm.

Migration solution to be used in the electrophoresis method relevant to the present invention is not particularly limited, and any solution commonly to be used in this field may be used. In the case of the capillary zone electrophoresis method, specifically the migration solution includes, for example, a buffer solution of pH 5 to 10, preferably pH 6 to 8, and the buffer solution can specifically include but not limited to, for example, a lactate buffer, a citrate buffer, an acetate buffer, a succinate buffer, a glycine buffer solution, a phthalate buffer, a phosphate buffer, a triethanolamine buffer, a borate buffer, a glycine buffer, a barbiturate buffer, a tris (hydroxymethyl)aminomethane-hydrochloride buffer solution, a tartrate buffer solution, a borate buffer solution, and the like. In addition, in the case of the capillary gel electrophoresis method, the migration solution includes the one where a polymer, for example, polyether such as, for example, polyethylene oxide (polyethylene glycol), polypropylene oxide; polyalkyleneimine such as, for example, polyethyleneimine; polyacrylic acid-based polymer such as, for example, polyacrylic acid, polyacrylate ester, polymethyl methacrylate; polyamide-based polymer such as, for example, polyacrylamide, polymethacrylamide; polymethacrylic acid-based polymer such as, for example, polymethacrylic acid, polymethacrylate ester, polymethyl methacrylate; polyvinyl-based polymer such as, for example, polyvinyl acetate, polyvinyl pyrolidone, polyvinyl oxazolidone; water-soluble hydroxyl polymer such as, for example, pullulan, elusinan, xanthan, dextran, guagum; water-soluble cellulose compound such as, for example, methylcellulose, hydroxyethylcellulose, hydroxypropylcellulose, and the like; derivatives thereof; copolymers containing plural kinds of monomer units constituting these polymers; and the like is added to the buffer solutions to be used as a migration solution for the above-described capillary zone electrophoresis. It should be noted that the above-described polymers may be added in a combination of two or more kinds. In addition, molecular weight of the above-described polymers as mentioned above is usually 500 Da to 6000 kDa, preferably 1 to 1000 kDa, and more preferably 100 to 100 kDa. In addition, concentration of the above-described polymers may be appropriately selected from a range usually used in this field, and is usually 0.01 to 40% (W/V), preferably 0.01 to 20% (W/V), and more preferably 0.1 to 10% (W/V). It should be noted that viscosity of the buffer solution for migration when the above-described filler is added to the buffer solution for migration is usually 2 to 1000 centipoise, preferably 5 to 200 centipoise, and more preferably 10 to 100 centipoise.

The above-described migration solution may contain a substance to reduce an effect of electroosmotic flow such as, for example, polyacrylamide, polyethylene glycol, polyethyleneimine, fluorine-containing aromatic hydrocarbon, sugars, and the like, and concentration thereof may be set in a range usually to be used in this field.

Since voltage at migration in the electrophoresis method relevant to the present invention varies depending on migration solution, equipment to be used, or the like, the voltage may be appropriately set in a range to be usually used in this field.

Method for introducing a sample, compound [1] of an internal standard substance of the present invention or the anion-group-containing compound relevant to the present invention, in the electrophoresis method relevant to the present invention, is not particularly limited, and may be a method usually used in this field. The method includes, for example, aspiration method, pressurization method, electric introduction method, and the like. Among them, pressurization method is preferable. It should be noted that the internal standard substance relevant to the present invention may be introduced by either a method in which the internal standard substance is dissolved in a sample in advance or a method in which a sample and a solution containing the internal standard substance are introduced separately. Amount to be introduced of the internal standard substance varies depending on conditions such as internal diameter and length of capillary, type and sensitivity of detector, or the like, but usually the same amount as injection volume of a sample is used. It should be noted that introduction of the above-described sample or the internal standard substance relevant to the present invention may be carried out by concentrating by a known isotachophoresis (ITP) and thereafter introducing the concentrate to the capillary electrophoresis as it is. In this case, for example, when microchip electrophoresis is used, it is desirable to carry out the ITP electrophoresis and the capillary electrophoresis continuously using a chip in which the ITP electrophoresis and the capillary electrophoresis are connected each other.

The above-described sample is not particularly limited, and the sample may be a solution containing the above-described analyte. Specifically, the sample includes, for example, body fluid such as serum, plasma, spinal fluid, joint fluid, lymph fluid; excrement such as urine and faces; sample derived from living organism such as sputum, pus, substance derived from skin; environmental sample such as, for example, food, beverage, tap water, sea water, lake water, river water, factory effluent, washing water for semiconductor, cleaning water after cleansing medical devices, and the like; and processed liquid obtained by reconstituting by appropriately dissolving these substances in water, a buffer solution usually to be used in this field such as, for example, a Tris buffer, a phosphate buffer, a veronal buffer, a borate buffer, a Good's buffer; and the like.

The electrophoresis method relevant to the present invention is carried out specifically, for example, by filling a capillary having internal diameter of 50 to 100 μm and length of 1 to 10 cm with Tris-HCl buffer containing, for example, 0.1 to 1.0% polydimethylaminoethyl methacrylate, 1 to 5% glycerol, and 0.01 to 0.1% BSA, introducing a sample containing a kind of internal standard substance by a pressurizing method at 1 to 10 psi for 30 to 60 seconds into the capillary, then introducing other internal standard substances into the capillary by a pressurizing method at 1 to 10 psi for 30 to 60 seconds, subsequently subjecting to electrophoresis by applying a voltage of, for example, 1000 to 3000 V for 10 to 60 minutes, and measuring by a detector such as fluorescence detector and UV detector.

The measurement method relevant to the present invention is performed by carrying out the electrophoresis under such conditions as mentioned above, and measuring migration states of an analyte and the internal standard substances using a detector such as fluorescence detector, UV detector, and the like to obtain an electropherogram, identifying peaks of the internal standard substances in said electropherogram, after that identifying a peak of analyte from a migration time thereof, and the like.

More specifically, for example, when an analyte in a sample is measured using two internal standard substances, electrophoresis for the internal standard substances and a standard substance of the analyte is carried out in advance, and migration times of two internal standard substances and the analyte, ratio of migration times between respective internal standard samples, and ratios of migration times between the internal standard substances and the analyte are measured. Subsequently, electrophoresis of the sample and the analyte are carried out under the same conditions, and peaks of two internal standard substances are identified from their migration times and the ratios of migration times between respective internal standard substances obtained in advance. Finally, peak of the analyte is identified from migration times of said two internal standard substances and ratios of migration times between respective internal standard substances and the analyte obtained in advance.

In addition, the compound of the present invention can be used as a labeling substance. In this case, a reaction activation group which can bind to a substance to be labeled may be introduced to the compound of the present invention, and said reaction activation group, introduction method thereof, and the like include the methods usually to be used in this field.

Hereinafter, the present invention will be explained further more specifically using Examples and Comparative Examples, but the present invention is not limited to them in any way.

EXAMPLES

Example 1

Synthesis of Compound of the Present Invention (15)

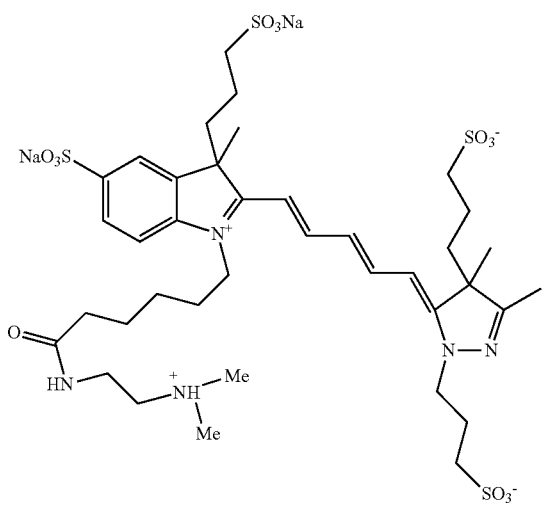

*Me = methyl group (1) Synthesis of Indolenine Compound (8)

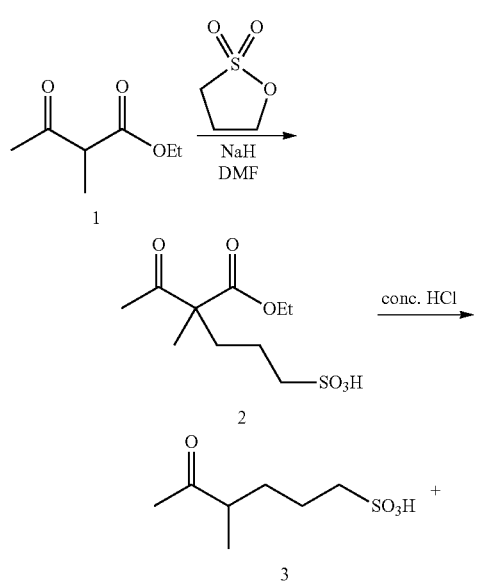

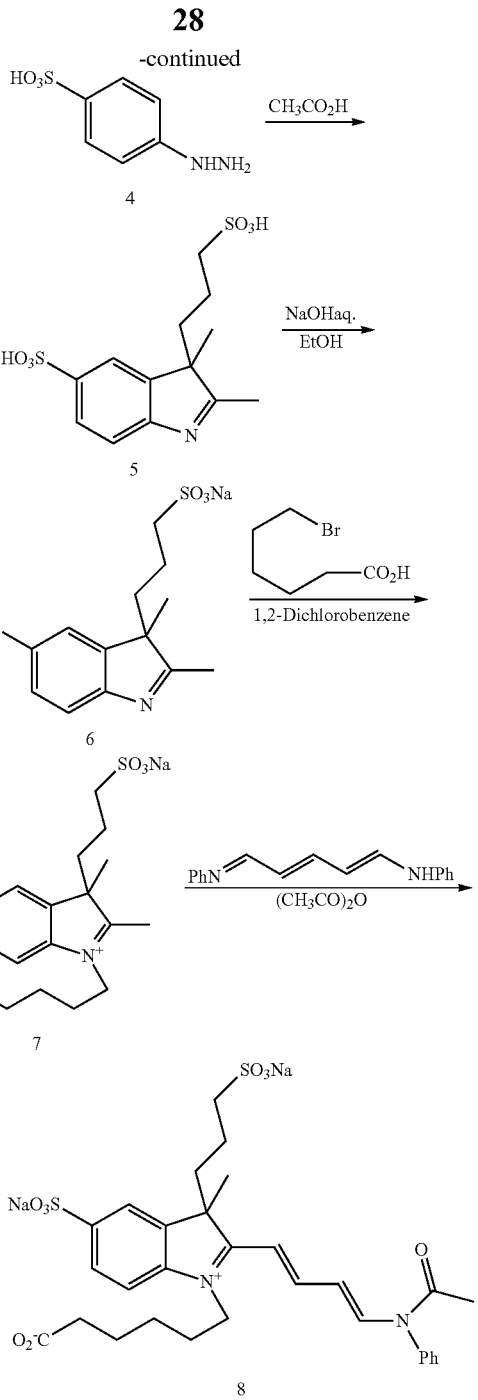

*Et = ethyl group, Ph = phenyl group

[Synthesis of Compound (2)]

Ethyl-2-methylacetoacetate (1) (25.0 g, 0.173 mol), 1,3-propanesultone (23.3 g, 0.190 mol) and sodium hydride (8.5 g, 0.208 mol) were added into N,N-dimethylformamide (DMF) (80 ml), and the solution was reacted with stirring at 90° C. overnight. After completion of the reaction, the solvent was distilled off under reduced pressure, and the residual mixture was washed twice by adding water (200 ml) and diethyl ether (200 ml). After that, the aqueous layer part was distilled off under reduced pressure to obtain compound (2) (42.1 g, yield: 91%).

[Synthesis of Compound (3)]

Compound (2) (40.5 g, 0.152 mol) was reacted in concentrated hydrochloric acid (60 ml) with stirring at 100° C. for 3 hours. After completion of the reaction, the solvent was distilled off under reduced pressure, and the product was purified by using silica gel column chromatography (eluate: methanol) to obtain compound (3) (16.6 g, yield: 56%).

[Synthesis of Compound (5)]

Compound (3) (10.0 g, 0.051 mol) and compound (4) (12.9 g, 0.066 mol) in acetic acid (50 ml) were heated under reflux at 120° C. for 4 hours. After completion of the reaction, the solvent was distilled off under reduced pressure, and the product was purified by using reverse phase column chromatography (eluate: water) to obtain compound (5) (11.5 g, yield: 65%).

Physical property data: IR (KBr) 3450, 1196

[Synthesis of Compound (6)]

Compound (5) (11.5 g, 0.033 mol) was dissolved in water (50 ml) and ethanol (50 ml), and the solution was reacted with stirring at room temperature for 4 hours. After completion of the reaction, the solvents were distilled off under reduced pressure, and the product was purified by using reverse phase column chromatography (eluate: water) to obtain compound (6) (10.3 g, yield: 80%).

Physical property data: Mass (nega=346)

IR (KBr) (cm$^{-1}$): 3444, 1193

[Synthesis of Compound (7)]

Compound (6) (10.0 g, 0.026 mol) and 6-bromohexanoic acid (9.97 g, 0.052 mol) were dissolved in 1,2-dichlorobenzene (100 ml), and the solution was reacted with stirring at 120° C. overnight. After completion of the reaction, the solvent was distilled off under reduced pressure, and the residual mixture was washed with ethyl acetate 3 times to obtain compound (7) (11.5 g, yield: 89%).

Physical property data: Mass (nega=460)

IR (KBr) (cm$^{-1}$): 3446, 1723, 1194

[Synthesis of Compound (8)]

Compound (7) (1.5 g, 2.967 mmol) and malonaldehydedianilide hydrochloride (0.77 g, 2.967 mmol) were dissolved in acetic anhydride (20 ml), and the solution was reacted with stirring at 120° C. for 1 hour. After completion of the reaction, the solvent was distilled off under reduced pressure, and the product was purified by using reverse phase column chromatography (eluate: 10% acetonitrile/water solution to obtain indolenine compound (8) (0.18 g, yield: 10%).

Physical property data: Mass (nega: posi=631: 633)

IR (KBr) (cm$^{-1}$): 3443, 1716, 1574, 1465, 1189

(2) Synthesis of Pyrazole Compound (12)

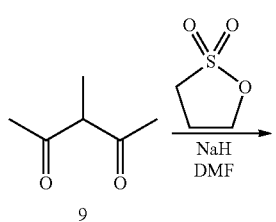

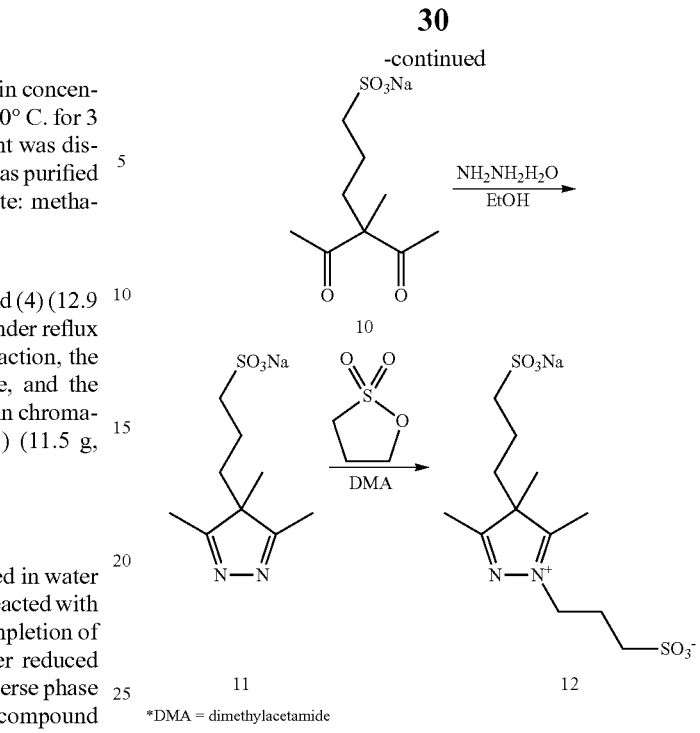

*DMA = dimethylacetamide

[Synthesis of Compound (10)]

A solution of 3-methyl-2,4-pentandione (compound (9)) (15.0 g, 0.13 mol), 1,3-propanesultone (16.1 g, 0.13 mol) and sodium hydride (5.0 g, 0.208 mol) in DMF (100 ml) was reacted with stirring at 50° C. for 16 hours. After completion of the reaction, the solution was neutralized with 1N sodium hydroxide, and the solvent was distilled off under reduced pressure, and the residual mixture was washed twice by adding water (200 ml) and diethyl ether (200 ml). After that, the aqueous layer part was distilled off under reduced pressure to obtain pyrazole compound (10) (32.2 g, yield: 96%).

Physical property data: IR (KBr) (cm$^{-1}$): 3474, 1695, 1665, 1191

[Synthesis of Compound (11)]

Compound (10) (10.0 g, 0.042 mol) and hydrazine monohydrate (2.1 g, 0.042 mol) were dissolved in ethanol (150 ml), and the solution was reacted with stirring at 80° C. for 3 hours. After completion of the reaction, the solvent was distilled off under reduced pressure, and the product was purified by using silica gel column chromatography (eluate: methanol/chloroform=1/1) to obtain compound (11) (9.0 g, yield: 92%).

Physical property data: IR (KBr) (cm$^{-1}$): 3421, 1195

[Synthesis of Compound (12)]

Compound (11) (4.8 g, 0.019 mol) and 1,3-propanesultone (2.5 g, 0.02 mol) were dissolved in dimethylacetamide (30 ml), and the solution was stirred at 140° C. for 4 hours. After completion of the reaction, ethyl acetate (200 ml) was added, and precipitated crystal was filtered to obtain pyrazole compound (12) (5.3 g, yield: 76%).

Physical property data: Mass (nega=352)

IR (KBr) (cm$^{-1}$): 3446, 1194

(3) Syntheses of Indolenine Compound-Pyrazole Compound Complexes (13) to (15)

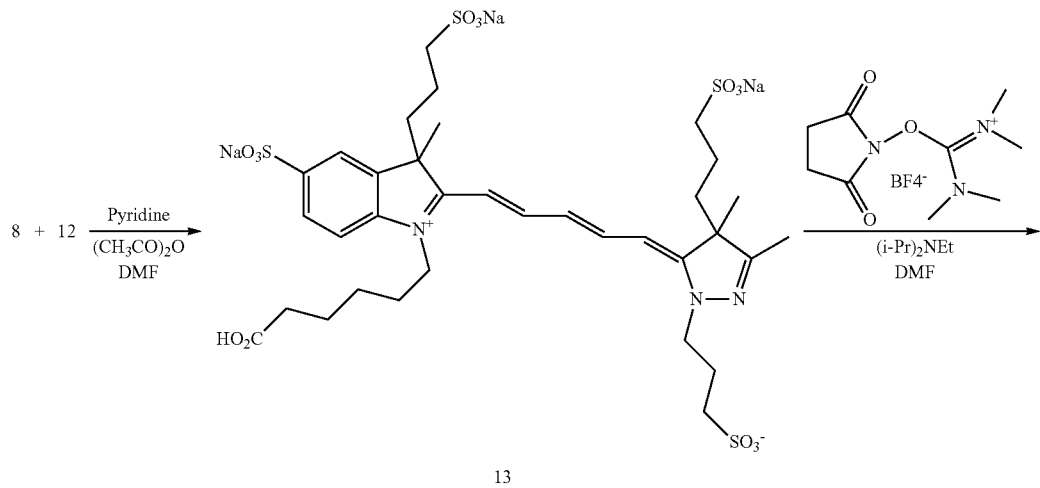

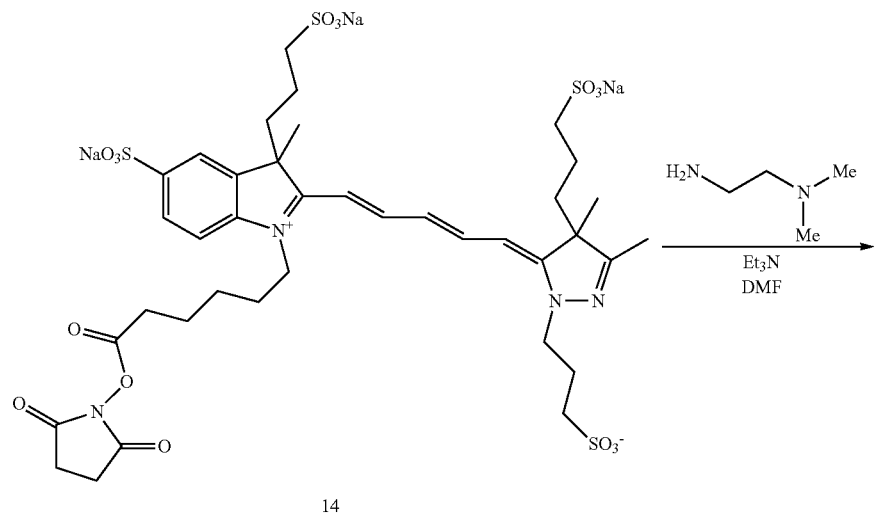

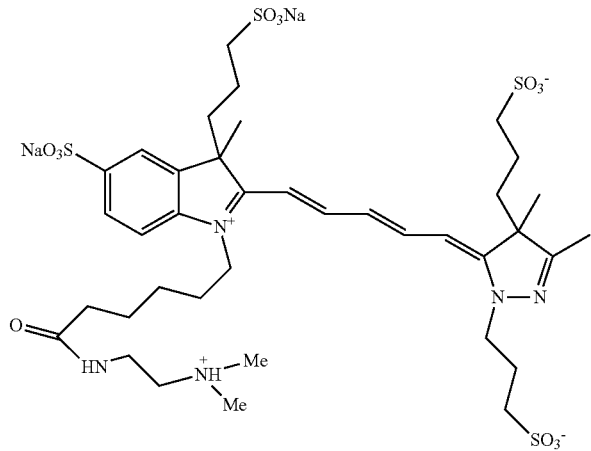

[Synthesis of Compound (13)] (a Known Compound)

Indolenine compound (8) (0.1 g, 0.158 mmol) obtained in Example 1-(1) and pyrazole compound (12) (0.17 g, 0.474 mmol) obtained in Example 1-(2) were dissolved in DMF (2 ml), and pyridine (1 ml) and acetic anhydride (0.5 ml) were further added thereto. The solution was stirred at 80° C. for 1 hour. After completion of the reaction, the solvent was distilled off under reduced pressure, and the product was purified by using reverse phase column chromatography (eluate: 10% aqueous methanol solution) and Sephadex LH-20 [produced by GE Healthcare Bioscience Co., Ltd. (former name: Amersham Bioscience Co. Ltd.)] (eluate: methanol) to obtain compound (13) (15 mg, yield: 12%).

Physical property data: Mass (nega=850)

Fluorescence characteristics of compound (13) are shown below.

| | |
|---|---|
| Maximum absorption wavelength (λmax) | 634 nm |
| Molar absorption coefficient (ε) | 230,000 M$^{-1}$cm$^{-1}$ |
| Maximum excitation wavelength [Ex(max)] | 635 nm |
| Maximum fluorescence wavelength [Em(max)] | 655 nm |

[Synthesis of Compound (14)]

Compound (13) (13 mg, 0.015 mmol) was dissolved in DMF (0.6 ml), and 2-succinimide-1,1,3,3-tetramethyluronium tetrafluoroborate (TSTU) (46 mg) and N-ethyldiisopropylamine [(i-Pr)$_2$NEt] (600 µl) were added thereto. The solution was stirred at room temperature for 1 hour. After completion of the reaction, the product was precipitated by adding ethyl acetate (15 ml) and centrifuged to obtain compound (14) (13 mg, yield: 90%).

Physical property data: Mass (nega=947)

[Synthesis of Compound (15)] (a Compound of the Present Invention)

Compound (14) (7 mg) was dissolved in DMF (0.5 ml), and N,N-dimethylaminoethylamine (10 mg) and triethylamine (Et$_3$N) (2 µl) were added thereto. The solution was stirred for 3 hours. After completion of the reaction, the solvent was distilled off under reduced pressure, and the product was purified by using preparative reverse phase column to obtain compound (15) (3.2 mg).

Physical property data: Mass (nega=933)

Fluorescence characteristics of compound (15) are, shown below.

| | |
|---|---|
| Maximum absorption wavelength (λmax) | 634 nm |
| Molar absorption coefficient (ε) | 230,000 M$^{-1}$cm$^{-1}$ |
| Maximum excitation wavelength [Ex(max)] | 635 nm |
| Maximum fluorescence wavelength [Em(max)] | 655 nm |

Example 2

Measurement of Fluorescence Intensity of the Compound of the Present Invention

Relative fluorescence intensities of known compound (13) and compound (15) of the present invention were roughly estimated.

Firstly, from a fluorescence intensity of known compound (13), a fluorescence intensity per 1 µl thereof was measured, and then a relative fluorescence intensity of the compound of the present invention was roughly estimated, and the fluorescence intensity of the known compound is 100.

Known compound (13) was dissolved in purified water (1 mL). This solution was diluted by 200 times with 50 mM phosphate buffer (pH 7.5), and OD value was measured. Subsequently, compound (15) of the present invention obtained in Example 1-(1) was dissolved in purified water (1 mL), and this solution was diluted with 50 mM phosphate buffer (pH 7.5) so that OD value thereof became equivalent to that of known compound (13). In this time, a relative fluorescence intensity of the following compound (15) of the present invention was roughly estimated, provided that a fluorescence intensity per 1 unit of OD value of known compound (13) is 100. Results are shown in Table 2.

TABLE 2

| Compound (fluorescent dye) | | Relative fluorescence intensity [fluorescence intensity of known compound (13) = 100] |
|---|---|---|
| Example 1 | Compound (15) of the present invention | 100 |
| Comparative Example 1 | Known compound (13) | 100 |

As obvious from the results of Table 2, it was found that compound (15) of the present invention showed the same fluorescence intensity as known compound (13).

Experimental Example 1

Separation and Measurement of AFP

Separation and measurement of AFP were carried out using the compound of the present invention as an internal standard substance in an electrophoresis.

[Analyte (Antigen)]

α-fetoprotein (AFP) (produced by Wako Pure Chemical Industries, Ltd.)

[Mobility Change Binding Substance (DNA-Labeled Antibody)]

According to the procedure shown in FIG. 1, a DNA-bound anti-AFP antibody Fab' fragment was prepared.

That is, firstly, a 250 bp DNA fragment introduced with NH$_2$ group in 5' terminal was purified by a common method (purified terminally-aminated. DNA), subsequently the NH$_2$ group introduced in this DNA fragment was reacted with a succinimide group of sulfosuccinimidyl 4-(p-maleimidephenyl)butylate (Sulfo-SMPB) linker (a linker having a succinimide group and a maleimide group, produced by Pierce Biotechnology, Inc.) by a common method, and then unreacted linker was removed by subjecting to gel filtration treatment, to obtain a linker-bound 250 bp DNA fragment. The obtained linker-bound 250 bp DNA fragment was reacted with anti-AFP antibody WA1 Fab' fragment prepared by using anti-AFP antibody WA1 (produced by Wako Pure Chemical Industries, Ltd.) according to a common method in advance. The obtained product was purified using DEAE column, respectively, to prepare an anti-AFP antibody WA1 Fab' fragment to which a 250 bp DNA fragment was bound (250 bp DNA-labeled antibody).

[Labeled Binding Substance (Fluorescence Labeled Antibody)]

Anti AFP antibody WA2 (produced by Wako Pure Chemical Industries, Ltd.) which recognized different epitope of AFP from WA1 was treated by a common method to prepare an anti-AFP antibody WA2 Fab' fragment, and then a fluorescent substance HyLyte 647 (produced by AnaSpec, Inc.) was introduced into an amino group of said fragment by a common method, to prepare a HyLyte 647-labeled anti-AFP abtibody WA 2 Fab' fragment (fluorescence labeled antibody).

[Internal Standard Substance]

As internal standard substance 1, known compound (13) (an intermediate of the compound of the present invention) obtained in Example 1 was used.

As internal standard substance 2, compound (15) of the present invention obtained in Example 1 was used.

[Capillary Chip]

A capillary chip having a layout shown in FIG. 2 was prepared as described below according to the method described in "Technology and applications of micro chemical chip, Takehiko Kitamori, et al., 2004 (Maruzen Co., Ltd.)". That is, a photoresist film was made on a Si deposited on a quartz substrate.

Figure 2:
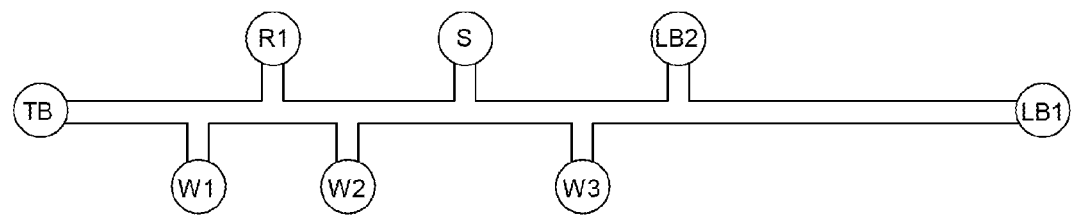
[FIG. 2]

Exposure was given to this photoresist using a mask having the capillary design (layout) illustrated in FIG. 2, and then development was carried out. Si in the area where photoresist was removed by the development was removed by sputtering, after that, wet etching was carried out using a hydrogen fluoride solution to make a capillary channel groove (capillary) on the quartz substrate. After removing photoresist and Si films remained on the quartz substrate, said quartz substrate and a cover plate having holes (wells) as liquid reservoirs were laminated by HF connection method to make a capillary chip.

It should be noted that, in FIG. 2, TB represents a well for introducing trailing buffer, LB1 and LB2 represent wells for introducing leading buffer, S represents a well for introducing sample for migration, R1 represents a well for introducing test solution (250 bp DNA-labeled antibody-containing solution), W1, W2 and W3 represent wells for drain, respectively.

[Electrophoresis]

(1) Leading Buffer

A 75 mM Tris-HCl buffer (pH 7.5) containing 0.6% (w/v) of polydimethylacrylamide (pDMA), 3% (w/v) of glycerol, 75 mM of NaCl, 0.01% of bovine serum albumin (BSA) and 4 mg/ml of LCA was used as a leading buffer.

(2) Trailing Buffer

A 75 mM Tris buffer containing 6% (w/v) of pDMA, 3% (w/v) of glycerol, 0.01% of BSA and 125 mM of HEPES was used as a trailing buffer.

(3) Sample for Migration

A 75 mM Tris-HCl buffer (pH 7.5) containing 0.6% (w/v) of polydimethylacrylamide (pDMA), 3% (w/v) of glycerol, 75 mM of NaCl, 0.01% of BSA and 3.6 mM of MES was used as a sample buffer, and 1 µL of serum containing 100 µM of AFP, 1 µL of a mixture of 1 µM of fluorescence-labeled antibody and 1 nM of WAKO-635 fluorescent dye, and 8 µL of the sample buffer were mixed in a 0.5 mL tube, to prepare 10 µL of reaction liquid.

The reaction liquid was placed on ice to allow an antigen-antibody reaction to progress for about 30 minutes, to form a fluorescence-labeled antibody-AFP immune complex. It should be noted that final concentration of the fluorescence-labeled antibody was 100 nM.

The obtained immune complex-containing reaction liquid was used as a sample for migration.

(4) Test Solution (250 bp DNA-Labeled Antibody-Containing Solution)

A leading buffer containing 100 nM of 250 bp DNA-labeled antibody and 1 nM of WAKO-635-$NH_2$ fluorescent dye (containing 50 mM of $Cl^-$ ion) was used as a test solution.

(5) Procedures of Electrophoresis a) Introduction of the Sample for Migration and the Test Solution In FIG. 2, 10 µL of the sample for migration (fluorescence-labeled antibody-AFP immune complex-containing solution) to S well (a well for introducing a sample for migration), 10 µL of the test solution (DNA-labeled antibody-containing solution) to R1 well (a well for introducing a test solution), 10 µl, of the leading buffer to LB1 well and LB2 well, and 10 µL of the trailing buffer to TB well were added dropwise, respectively. The sample for migration, the test solution, the leading buffer and the trailing buffer were introduced into channels by applying a pressure of −5 psi among W1 (a well for drain)-W2 (a well for drain)-W3 (a well for drain) for 30 seconds. Arrangement of the sample for migration and the test solution in a capillary is schematically shown in FIG. 3.

Figure 3:
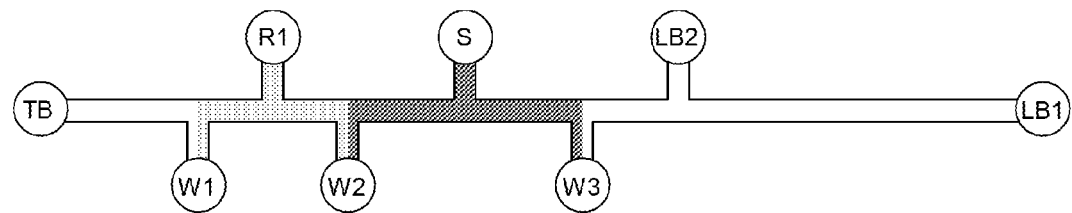
[FIG. 3]

It should be noted that, in FIG. 3, the shaded area represents a part occupied with the sample for migration, and the point part represents a part occupied with the test solution.

b) ITP (Reaction, Concentration, Separation) Detection

By applying a voltage of 3000 V between TB well and LB1 well in FIG. 3, the 250 bp DNA-labeled antibody in the test solution was contacted with fluorescence-labeled antibody-AFP immune complex in the sample for migration at 30° C., to form an immune complex of fluorescence-labeled antibody-AFP-250 bp DNA-labeled antibody, which was then concentrated by isotachophoresis (ITP).

It should be noted that reaction time was about 100 seconds (as a time for 250 bp DNA-labeled antibody to pass through the zone of the sample for migration (the shaded zone). After the immune complex was subjected to isotachophoresis to LB2 and its passing through LB2 was judged from a change in voltage, negative electrode was switched from TB to LB2, and the capillary gel electrophoresis (CGE) was further carried out until a peak of the fluorescence-labeled antibody-AFP-250 bp DNA-labeled antibody immune complex was detected in the detection part (a capillary part 2 cm apart from the LB2 channel crossing part).

It should be further noted that detection was carried out by measuring over time an intensity of fluorescence generated by 635 nm laser excitation in the capillary part 2 cm apart from the LB2 channel crossing part, by a fluorescence microscope (BX-50, produced by KS Olympus Co., Ltd.).

[Results]

Figure 4:
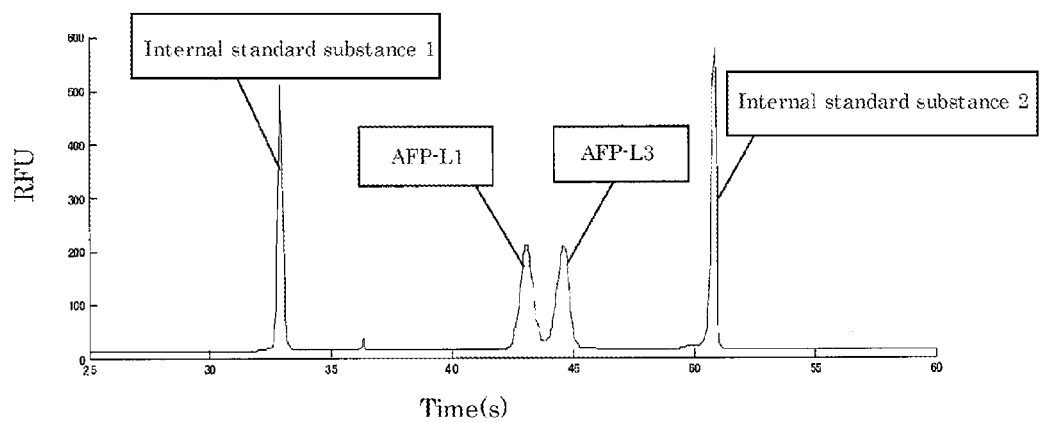
[FIG. 4]

An electrophoretic profile (electrophoretic chromatogram) when the sample for migration was used is shown in FIG. 4. It should be noted that, in FIG. 4, the vertical axis represents fluorescence intensity, and the horizontal axis represents retention time, respectively.

From the results in FIG. 4, it was found that by carrying out electrophoresis using internal standard substances 1 and 2 relevant to the present invention as mentioned above, peaks of AFP-L1 and AFP-L3 of measuring object became to appear between both peaks of the internal standard substances, and thereby both peaks could be identified easily.

Example 3

Separation and Measurement of PIVK II

[Analyte (antigen)]

PIVK II was prepared according to the method described in Poser J W, Price P A, J. Biol. Chem. 1979, Jan. 25; 254(2): 431-6.

[Mobility Change Binding Substance (DNA-Labeled Antibody)]

Preparation of the substance was carried out in the same way as in Example 1 except that PIVKA H Fab' fragment was used instead of anti-AFP antibody WA1 Fab' fragment, to obtain an anti-PIVKA II antibody Fab' fragment (250 bp DNA-labeled antibody).

[Labeled Binding Substance (Fluorescence-Labeled Antibody)]

An anti-prothrombin antibody prepared by a common method was treated to make an anti-prothrombin antibody Fab' fragment, and by introducing a fluorescent substance HiLyte 647 (produced by AnaSpec, Inc.) by a common method to an amino group of said fragment, HiLyte 647-labeled anti-prothrombin antibody Fab' fragment (fluorescence-labeled antibody) was prepared.

[Internal Standard Substance]

The same internal standard substances 1 and 2 as in Example 1 were used.

[Capillary Chip]

The same one as in Example 1 was used.

[Electrophoresis]

(1) Leading Buffer

The same one as in Example 1 was used.

(2) Trailing Buffer

The same one as in Example 1 was used.

(3) Sample for Migration

A 75 mM Tris-HCl buffer (pH 7.5) containing 0.6% (w/v) of polydimethylacrylamide (pDMA), 3% (w/v) of glycerol, 75 mM of NaCl, 0.01% of BSA and 3.6 mM of MES was used as a sample buffer, and 1 µL of serum containing 100 µM of PIVKA II, 5 µL of a mixture of 1 µM of fluorescence-labeled antibody and 1.4 nM of internal standard substance 1, and 8 µL of the sample buffer were mixed in a 0.5 mL tube, to prepare a reaction liquid.

The reaction liquid was placed on ice to allow an antigen-antibody reaction to progress for about 30 minutes, to form a fluorescence-labeled antibody —PIVKA 11 immune complex. It should be noted that final concentration of the fluorescence-labeled antibody was 100 nM.

The obtained immune complex-containing reaction liquid was used as a sample for migration.

(4) Test Solution (250 bp DNA-Labeled Antibody-Containing Solution)

A leading buffer containing 200 nM 250 bp DNA-labeled antibody and 140 pM internal standard substance 2 (containing 50 mM Cl⁻ ion) was used as a test solution.

(5) Procedures of Electrophoresis

The sample for migration and the test solution were introduced in the same way as in Example 1, and after concentrating by ITP and then carrying out CGE, an intensity of fluorescence generated by 635 nm laser excitation in the capillary part 2 cm apart from the LB2 channel crossing part was measured over time using a fluorescence microscope (BX-50, produced by Olympus Co., Ltd.).

[Results]

Figure 5:
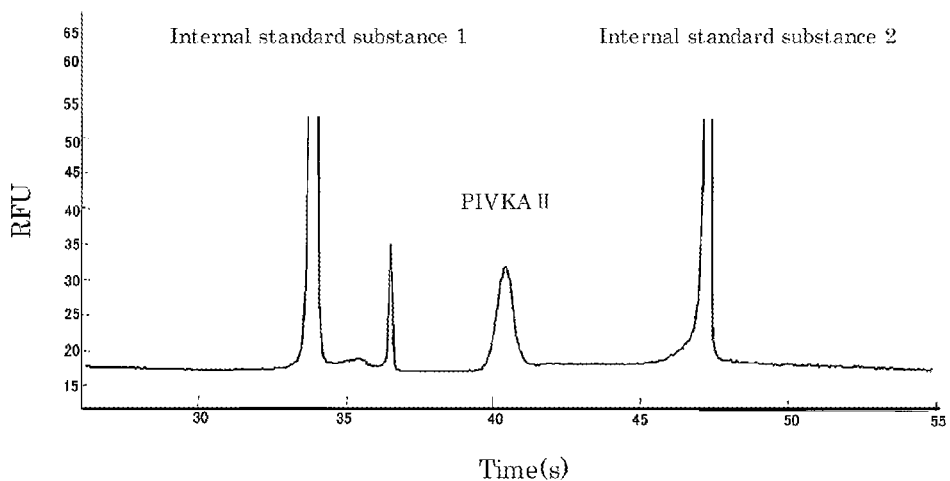
[FIG. 5]

An electrophoretic profile (electropherogram) when the sample for migration was used is shown in FIG. 5. It should be noted that in FIG. 5, the vertical axis represents fluorescence intensity, and the horizontal axis represents retention time, respectively.

From the results in FIG. 5, it was found that by carrying out electrophoresis using internal standard substances 1 and 2 relevant to the present invention as mentioned above, a peak of PIVKA II was allowed to locate between both peaks of the internal standard substances, and thereby the peak of PIVKA H could be identified easily.

The invention claimed is:

1. A compound represented by the general formula [1] or a salt thereof:

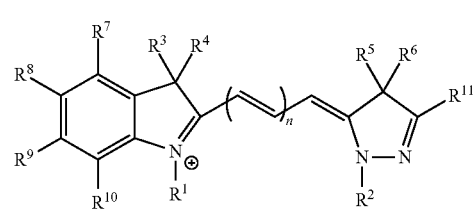

[1]

wherein $R^1$ to $R^6$ each independently represent:
an alkyl group;
an alkyl group substituted by a group represented by the general formula [101]:

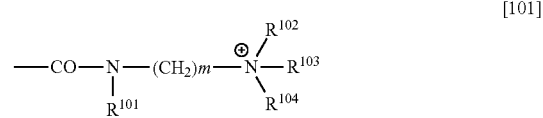

[101]

wherein $R^{101}$ to $R^{104}$ each independently represent a hydrogen atom or a $C_1$ to $C_3$ alkyl group and m represents an integer from 2 to 6, or two or three of $R^{102}$ to $R^{104}$ together with a nitrogen atom to which they are bound may form a heterocyclic ammonium cation;
an alkyl group substituted by a group represented by the general formula [2] and which optionally contains an amide bond:

$$—COOR^{12}$$ [2]

wherein $R^{12}$ represents a hydrogen atom, a $C_1$ to $C_{10}$ alkyl group, an alkali metal atom, an organic ammonium ion, or an ammonium ion or anion; or
an alkyl group substituted by a group represented by the general formula [3] and which optionally contains an amide bond:

$$—SO_3R^{13}$$ [3]

wherein $R^{13}$ represents a hydrogen atom, an alkali metal atom, an organic ammonium ion, an ammonium ion or anion;
$R^7$ to $R^{10}$ each independently represent an alkyl group, an alkynyl group, an aryl group, an alkoxy group, an aryloxy group, an alkylsulfonyl group, an arylsulfonyl group, an amino group, a group represented by the general formula [2], a group represented by the general formula [3], a halogen atom, a hydrogen atom, a hydroxyl group, a cyano group or a nitro group;
$R^{11}$ represents a hydrogen atom, an alkyl group, an alkynyl group or an aryl group, and n represents an integer from 0 to 3, wherein at least one of $R^1$ to $R^6$ is an alkyl group substituted by a group represented by the general formula [101].

2. The compound according to claim 1, wherein the compound represented by the general formula [1] is a compound represented by the following general formula [1']:

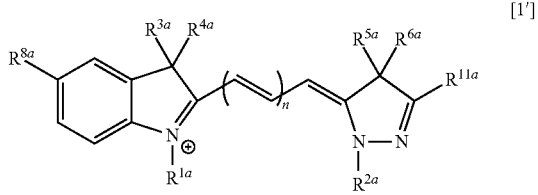

[1']

wherein $R^{1a}$ to $R^{6a}$ each independently represent:
an alkyl group;
an alkyl group substituted by a group represented by the general formula [101];
an alkyl group substituted by a group represented by the general formula [2] ; or an alkyl group substituted by a group represented by the general formula [3],
$R^{8a}$ is a group represented by the general formula [3],
$R^{11a}$ represents an alkyl group, and
n represents an integer from 0 to 3,
wherein at least one of $R^{1a}$ to $R^{6a}$ is an alkyl group substituted by a group represented by the general formula [101]).

3. The compound according to claim 1, wherein $R^1$ or $R^2$ is an alkyl group substituted by a group represented by the general formula [101].

4. The compound according to claim 1, wherein the compound represented by the general formula [1] comprises 1 to 4 groups selected from a group consisting of a group represented by the general formula [3] and an alkyl group substituted by a group represented by the general formula [3].

5. The compound according to claim 4, wherein the compound represented by the general formula [1] comprises 4 groups represented by the general formula [3].

6. The compound according to claim 1, wherein $R^8$ is the group represented by the general formula [3], and either $R^1$ or $R^2$, either $R^3$ or $R^4$, and either $R^5$ or $R^6$ are an alkyl group substituted by the group represented by the general formula [3].

7. The compound according to claim 1, wherein one of $R^1$ or $R^2$ is a $C_1$ to $C_6$ alkyl group substituted by a group represented by the general formula [101], and the other is a $C_1$ to $C_5$ alkyl group substituted by a group represented by the general formula [3].

8. The compound according to claim 1, wherein $R^{101}$ is a hydrogen atom, and any one of $R^{102}$ to $R^{104}$ is a hydrogen atom and other two are alkyl groups.

9. The compound according to claim 1, wherein the group represented by the general formula [101] is a N,N-dimethylammonioethylcarbamoyl group.

10. The compound according to claim 1, wherein one of $R_3$ and $R_4$ is a $C_1$ to $C_5$ alkyl group substituted by a group represented by the general formula [3], and the other is a $C_1$ to $C_6$ alkyl group; and
one of $R_5$ and $R_6$ is a $C_1$ to $C_5$ alkyl group substituted by a group represented by the general formula [3], and the other is a $C_1$ to $C_6$ alkyl group.

11. The compound according to claim 1, wherein the compound represented by the general formula [1] is a compound represented by the following general formula [1-2]:

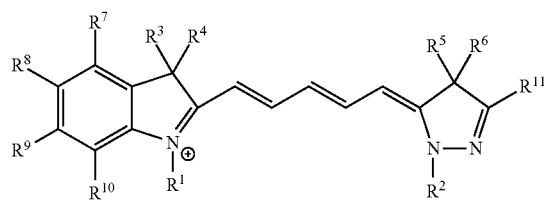

[1-2]

wherein $R^1$ to $R^{11}$ are the same as defined in claim 1.

* * * * *